(12) United States Patent
Goldfarb et al.

(10) Patent No.: US 12,070,407 B2
(45) Date of Patent: Aug. 27, 2024

(54) UPPER EXTREMITY ASSISTANCE DEVICE

(71) Applicant: Vanderbilt University, Nashville, TN (US)

(72) Inventors: Michael Goldfarb, Nashville, TN (US); Benjamin William Gasser, Nashville, TN (US); Daniel Alvin Bennett, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 86 days.

(21) Appl. No.: 18/060,029

(22) Filed: Nov. 30, 2022

(65) Prior Publication Data

US 2023/0092096 A1    Mar. 23, 2023

Related U.S. Application Data

(62) Division of application No. 16/614,935, filed as application No. PCT/US2018/034607 on May 25, 2018, now Pat. No. 11,534,321.
(Continued)

(51) Int. Cl.
    *A61F 5/01* (2006.01)
(52) U.S. Cl.
    CPC ...... *A61F 5/013* (2013.01); *A61F 2005/0134* (2013.01); *A61F 2005/0151* (2013.01);
    (Continued)

(58) Field of Classification Search
    CPC .............. A61F 5/013; A61F 2005/0134; A61F 2005/0151; A61F 2005/0155; A61F 2005/0158; A61F 2005/0188; B25J 9/0006
    See application file for complete search history.

(56) References Cited

U.S. PATENT DOCUMENTS 3,698,389 A    10/1972  Guedel
3,967,321 A     7/1976  Ryan
(Continued)

FOREIGN PATENT DOCUMENTS

WO    WO 0158392 A1     8/2001
WO    WO 2011/137904 A1  11/2011

OTHER PUBLICATIONS

International Search Report for International Application No. PCT/US2018/034607, mailed Aug. 24, 2018 (2 pages).
(Continued)

*Primary Examiner* — Tarla R Patel
(74) *Attorney, Agent, or Firm* — Nixon Peabody LLP

(57) ABSTRACT

In one embodiment, the orthotic device can include a powered hand portion, a switching element, and a controller. The wearer can interact with the switching element to generate input signals for adjusting an operation of the powered hand portion. The controller can receive the input signals and generate control signals to accordingly adjust the operation of the powered hand portion. In some embodiments, a powered hand portion can be comprised of a plurality of linkages and at least one powered actuator to assist with an opening and closing of the hand portion. The plurality of linkages can be operated by at least one electric motor with quick-connect elements to link onto fingers of a user. In some embodiments, an electrically-actuated clutch mechanism can be affixed to an upper arm section and a lower arm section of an orthotic device. The clutch mechanism can be configured into different positions.

7 Claims, 17 Drawing Sheets

Related U.S. Application Data

(60) Provisional application No. 62/511,153, filed on May 25, 2017.

(52) U.S. Cl.
CPC .............. *A61F 2005/0155* (2013.01); *A61F 2005/0158* (2013.01)

(56) References Cited

U.S. PATENT DOCUMENTS

| | | | |
|---|---|---|---|
| 5,800,561 | A | 9/1998 | Rodriguez |
| 5,848,979 | A | 12/1998 | Bonutti |
| 5,891,061 | A | 4/1999 | Kaiser |
| 7,473,234 | B1 | 1/2009 | Weltner |
| 8,100,844 | B2 | 1/2012 | DeHarde |
| 8,273,042 | B2 | 9/2012 | Lidolt |
| 9,844,447 | B2 * | 12/2017 | van der Merwe ........ A61F 2/68 |
| 2003/0223844 | A1 * | 12/2003 | Schiele .................. A63B 23/12 414/5 |
| 2005/0165337 | A1 | 7/2005 | Weiss |
| 2006/0161220 | A1 * | 7/2006 | Kobayashi ........... A61H 1/0277 601/33 |
| 2008/0071386 | A1 | 3/2008 | McBean |
| 2009/0326422 | A1 | 12/2009 | Hoffman |
| 2013/0072829 | A1 | 3/2013 | Fausti |
| 2014/0243721 | A1 | 8/2014 | Bryant |
| 2015/0173929 | A1 | 6/2015 | Kazerooni |
| 2015/0190246 | A1 * | 7/2015 | Ryu ........................ B25J 13/02 74/89.22 |
| 2015/0321341 | A1 * | 11/2015 | Smith ...................... A61H 3/00 623/57 |
| 2016/0051388 | A1 | 2/2016 | Goldfarb |

OTHER PUBLICATIONS

Written Opinion of International Searching Authority for International Application No. PCT/US2018/034607, mailed Aug. 24, 2018 (5 pages).

International Preliminary Report on Patentability for International Application No. PCT/US2018/034607, mailed Dec. 5, 2019 (7 pages).

Supplementary European Search Report in European Patent Application No. EP 18805530.5, mailed Dec. 15, 2020 (11 pages).

* cited by examiner

UPPER EXTREMITY ASSISTANCE DEVICE

CROSS-REFERENCE TO RELATED APPLICATIONS

This application is a divisional application of U.S. application Ser. No. 16/614,935 filed Nov. 19, 2019, which has been allowed; U.S. patent application Ser. No. 16/614,935 filed Nov. 19, 2019, is a U.S. National Stage Entry of International Application No. PCT/US2018/034607, filed May 25, 2018, which claims priority to and the benefit of U.S. Provisional Application No. 62/511,153, filed May 25, 2017 and entitled "Upper Extremity Assistance Device", the contents of which are herein incorporated by reference in their entirety.

FIELD OF THE INVENTION

The present invention relates to orthotic devices for upper extremities, and more specifically to orthotic devices for managing non-functional upper extremities.

BACKGROUND

A large number of persons commonly suffer from hemiparesis or hemiplegia. Persons with hemiparesis suffer from weakness on one side of the body. That is, the patient can move an arm, leg, and/or trunk associated with an impaired side of their body, but with reduced muscular strength. Persons with hemiplegia are afflicted with paralysis of the arm, leg, and/or trunk on the same side of the body. Hemiplegia and hemiparesis may be congenital, or they might be acquired conditions resulting from an illness, an injury, or a stroke.

Whether a person is suffering from hemiparesis or hemiplegia, the end result is extreme difficulty performing everyday tasks. In particular, many activities of daily living entail bimanual tasks, which either require or are greatly facilitated by the use of two hands. In many bimanual tasks, one arm and hand are used essentially to provide support or resistance, while the other arm and hand are used to provide power or movement. Examples include twisting a lid off of a jar, slicing a loaf of broad, turning the page of a book, taking currency out of a wallet, etc. Still other tasks use one or both arms to hold an object, but do not otherwise require motive power. Examples include holding a bag or briefcase (single-arm holding tasks), or holding a laundry basket (bimanual holding task).

SUMMARY

Embodiments of the invention concern orthotic devices for managing non-functional or diminished function upper extremities. A first exemplary embodiment concerns an orthotic device comprising a forearm section, a powered hand portion, a switching element, and a controller. The powered hand portion can be coupled to a distal end of the forearm section. The switching element can be configured to generate one or more input signals for adjusting operation of the powered hand portion. The controller can be configured to receive the input signals. Based on the input signals, the controller can generate control signals for the adjusting of the operation of the powered hand portion.

In some examples, the switching element can comprise a momentary switch for generating the input signals. In response to input signals which indicate a first temporary activation of the momentary switch, the controller can configure the control signals to cause the powered hand portion to alternate between an open position and a closed position.

In some examples, the controller can generate the control signals following a predetermined time delay. The predetermined time delay can commence upon release of the momentary switch after the first activation.

In some examples, the input signals can indicate one or more second temporary activations of the momentary switch within the predetermined time delay. In response, the controller can configure the control signals to cause the powered hand portion to alternate between the open position and the closed position with an amount of fore proportional to a number of the one or more second temporary activations.

In some examples, the controller can be configured to reset the predetermined time delay after each of the one or more second temporary activations.

In some examples, the input signals can indicate a continuous activation of the momentary switch for a first period of time. In response, the controller can configure the control signals to switch the controller to operate the powered hand portion using an alternate control mode. In other examples, the input signals can indicate a continuous activation of the momentary switch for a second period of time which is different than the first period of time. In response, the controller can configure the control signals to power off the powered hand portion.

In some examples, in the alternate control mode, the controller can configure the control signals to cause the powered hand portion to continuously cycle between the open position and closed position for a predetermined number of cycles.

In another example of the first embodiment, the switching element can comprise a toggle switch. The toggle switch can have a neutral position, a first switch position, and a second switch position. The first switch position can cause a first configuration of the input signals. The second switch position can cause a second configuration of the input signals. In response to the input signals being in the first configuration, the controller can configure the control signals to cause the powered hand portion to transition towards the closed position. In response to the input signals being in the second configuration, the controller can configure the control signals to cause the powered hand portion to transition towards the open position.

In some examples, the controller can generate the control signals following a predetermined time delay. The predetermined time delay can begin upon a return of the toggle switch to the neutral position.

In some examples, the controller can configure the control signals so that a force associated with at least one of the transition to the open position or the transition to the closed position is related to an amount of time that the toggle switch is maintained away from the neutral position.

In some examples, the powered hand portion can be in the closed position and the input signals can indicate successive momentary activations of the toggle switch to the first switch position. In response, the controller can configure the control signals to cause the powered hand portion to successively increment the closing force. In other examples, the input signals can indicate successive momentary activations of the toggle switch to the second switch position. In response, the controller can configure the control signals to cause the powered hand portion to successively decrement the closing force.

In some examples, the powered hand portion can be in the open position and the input signals can indicate a continuous activation of the toggle switch in the second switch position for a first period of time. In response, the controller can configure the control signals to switch the controller to operate the powered hand portion using an alternate control mode.

In some examples, the powered hand portion can be in the closed position and the input signals can indicate a continuous activation of the toggle switch in the first switch position for a first period of time. In response, the controller can configure the control signals to switch the controller to operate the powered hand portion using an alternate control mode.

In some examples, the controller can be in an alternate control mode. In the alternate control mode, the controller can configure the control signals to cause the powered hand portion to continuously cycle between the open position and the closed position for a predetermined number of cycles.

In some examples, the powered hand portion can be in the closed position and the input signals can indicate a continuous activation of the toggle switch in the first switch position for a second period of time. In some examples, the powered hand portion can be in the open position and the input signals can indicate a continuous activation of the toggle switch in the second switch position for a second period of time. In response to either of these situations, the controller can configure the control signals to power off the device.

In a second embodiment of the present disclosure, and orthotic device can comprise a forearm section and a powered hand portion. The powered hand portion can be coupled to a distal end of the forearm section. The powered hand portion can be comprised of a plurality of linkages. The powered hand portion can be comprised of at least one powered actuator to assist with an opening and closing of the hand portion.

In some examples of the second embodiment, the plurality of linkages can further comprise linkages configured to adjoin to portions of a hand.

In some examples of the second embodiment, the at least one powered actuator can further comprise at least one electric motor affixed to one of the plurality of linkages. The at least one electric motor can be rotatably coupled to at least one double pulley. A first pulley section can be wound with a first cable in a primary direction. A second pulley section can be wound with a second cable in an opposite direction. The first cable can pass along an anterior aspect of the plurality of linkages. The second cable cab pass along a posterior aspect of the plurality of linkages.

In some examples of the second embodiment, the device can further comprise a distal linkage and at least one digit-securing element. The digit-securing element can be comprised of at least a strapping element and a quick-connect base element. The quick-connect base element can be comprised of a convex surface. The convex surface can be configured for snapping into a mating set of receiving clips in the distal linkage.

In some examples of the second embodiment, the powered hand portion can further comprise a thumb portion. The thumb portion can comprise at least a thumb cup and a thumb rod. The thumb rod can comprise a first end and a second end. The first end can be clamped slidably and rotatably to a first linkage of the plurality of linkages. The second end can be clamped slidably and rotatably to the thumb cup.

In a third embodiment of the present disclosure, an orthotic device can comprise an upper arm section, a forearm section, at least one elbow joint, and at least one electrically-actuated clutch mechanism. The at least one elbow joint can rotatably couple the upper arm portion and the forearm section. The at least one electrically-actuated clutch mechanism can be comprised of at least one rotating member, at least one sliding member, and at least one bearing member.

In some examples, the at least one rotating member of the at least one electrically-actuated clutch can include at least one detent and can be affixed to a first arm section. The at least one sliding member of the at least one electrically-actuated clutch mechanism can slide through a second arm section, such that the at least one rotating member rotates relative to the at least one sliding member.

In some examples, the at least one sliding member can be slidably configured within the second arm section into either a first slider position or a second slider position. In the first slider position, the at least one sliding member can force the at least one bearing member into the at least one detent in the rotating member. In the second slider position, the sliding member can release the at least one bearing member from the at least one detent in the at least one rotating member.

In some examples, the at least one sliding member can be configured into the first slider position by a spring. The at least one sliding member can be configured into the second slider position by energizing a solenoid actuator.

In some examples, the at least one detent can be a radial aspect of the at least one rotating member. The at least one detent can be cylindrical or spherical in shape.

DETAILED DESCRIPTION

Figure 1:
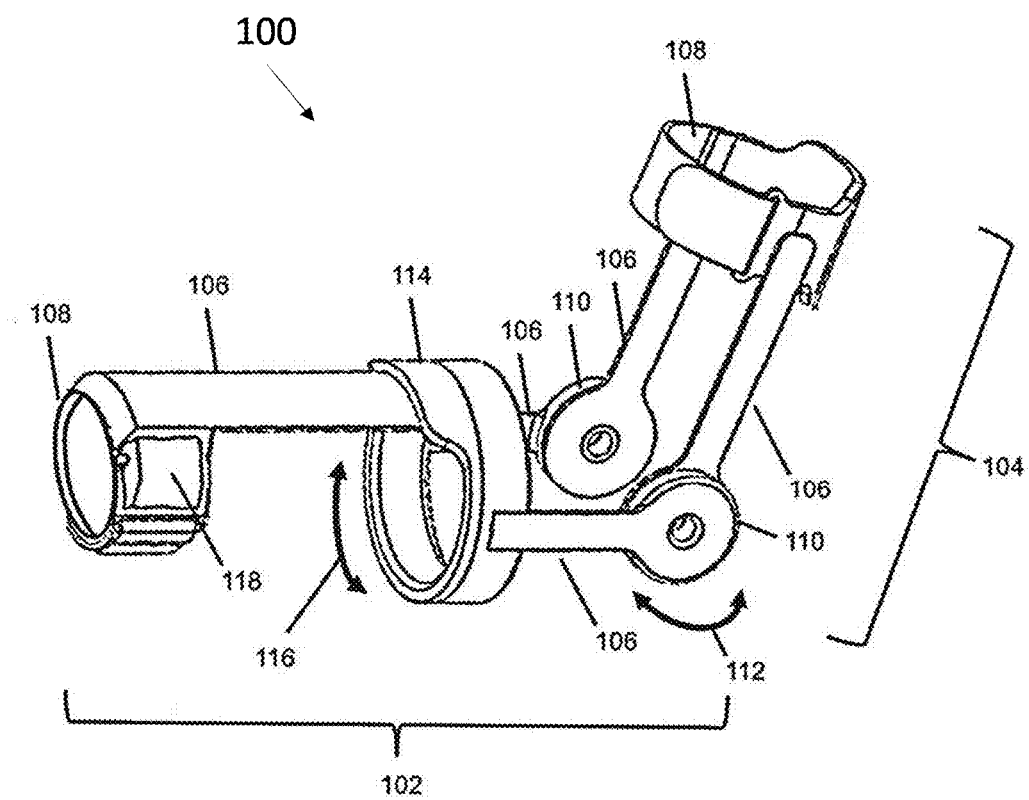
FIG. 1 shows an exemplary orthotic device useful for discussing various embodiments of the present disclosure.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

To address the issues faced by persons with people with upper extremity neuromuscular deficits, due to hemiplegia, hemiparesis, or other conditions, the present technology provides upper extremity assistance devices configured to allow such people greater mobility and use of their non-functional or paretic arm. In particular, an upper extremity assistance device in accordance with the present technology can be implemented as an orthotic device intended for people with one essentially functional arm (i.e., the non-paretic arm), and one essentially paretic arm, such as people with dense upper extremity hemiplegia, or with people with other neuromuscular impairments that present similarly (e.g., incomplete spinal cord injury, traumatic brain injury, or multiple sclerosis).

In accordance with the present technology, the orthotic device is worn on the paretic arm. In one embodiment, the orthotic device can include a powered hand portion, a switching element, and a controller. The wearer can interact with the switching element to generate input signals for adjusting an operation of the powered hand portion. The controller can receive the input signals and generate control signals to accordingly adjust the operation of the powered hand portion. The controller can configure the powered hand portion to grasp or release an object, or to alternate the powered hand between different postures. For example, the movement assistance for the hand portion can be configured to alternate the hand of the paretic arm between grasp and release postures.

In a second aspect of the present technology, a powered hand portion can include a plurality of linkages and at least one powered actuator to assist with an opening and closing of the hand portion. The plurality of linkages can be operated by at least one electric motor with quick-connect elements to link onto fingers of a user. In a third aspect of the present technology, an electrically-actuated clutch mechanism can be affixed to an upper arm section and a lower arm section of an orthotic device. The clutch mechanism can be configured into different positions. These aspects of the present technology allow for orthotic devices according to various embodiments of the present disclosure to be used for a variety of activities with complex instructions and abilities.

FIG. 1 shows an orthotic device 100 which is useful for describing various aspects of the present technology. The orthotic device 100 includes a forearm portion 102 and an upper arm portion 104, structural elements 106, and securing elements 108 in the forearm portion 102 and the upper arm portion 104, which attach the orthotic device 100 to the upper arm and forearm portions of the paretic arm. In FIG. 1, the securing elements 108 are arranged to attach the orthotic device 100 around the wrist of the paretic arm and around the biceps of the paretic arm. The orthotic device 100 also includes at least an elbow joint 110 that is normally locked to prevent motion 112 resulting in flexion or extension of the elbow of the paretic arm. The orthotic device 100 further includes a wrist joint 114. As shown in FIG. 1, the wrist joint can be situated at the proximal forearm, near the elbow joint 110. In general, the length of the structural elements 106 can be configured to be adjustable to allow a fit of the orthotic device to different users with difference arm lengths.

Although FIG. 1 is described as including a normally-locked joint associated with wrist pronation/supination, also referred to here as wrist rotation, the present technology is not limited in this regard. In other embodiments, the orthotic device 100 can include multiple normally-locked wrist degrees of freedom (e.g., wrist flexion/extension, ulnar/radial deviation, and pronation/supination).

In addition to the foregoing components, the orthotic device 100 also includes a release lever, button, or control 118. In the orthotic device, the release control 118 is positioned with the securing element 108 in the forearm portion 102. The release control 118 and the orthotic device are configured so that the elbow joint 110 and the wrist joint 104 are contemporaneously unlocked by grasping and squeezing the portion of the securing element 108 including the release control 118, near the anatomical wrist joint of the paretic limb. Thus, a user can reposition the paretic arm using their non-paretic arm.

In some embodiments, the release control 118 can be configured to pull at least one cable (not shown), which is routed along or within structural elements 106 and which releases a mechanical clutch mechanism (not shown) in joints 110 and 114 and enables free motion of these normally-locked joints. In another embodiment, the release control 118 can be an electrical switch wired (wires not shown) with one or more electrically-actuated clutches (not shown) in the joints 110 and 114, to simultaneously release the normally-locked joints. In another embodiment, a combination of mechanical and electrical release mechanisms is used. Regardless of the mechanism, the user can reposition the paretic arm into a desired pose. Once the release control 118 is released by user, the clutch mechanisms in joints 110 and 114 are re-engaged and the paretic arm is locked into the new pose.

As noted above, the mechanism by which the elbow joint 110 is unlocked can be mechanical or electrical. In embodiments with mechanical operation, activating the release control 118 situated at the distal forearm pulls a cable, which releases a clutch at the elbow joint 110 and the wrist rotation joint 114 of the orthotic device 100. The release control 118 can pull on multiple cables, which can release multiple clutch mechanisms situated in parallel, or can pull on a single cable, which releases multiple clutch mechanisms in series (i.e., daisy-chained together). Several clutch types will provide effective normally-locked joints that can be released via cable excursion, including friction clutch, dog clutch, wrapped spring clutch, and belt clutch variants. In embodiments with electrical operation, depressing the release control situated on the orthotic device at the distal forearm releases an electrically-actuated clutch, which releases the elbow joint 110 of the orthotic device 100. Several clutch types will provide effective normally-locked joints that can be released via electrical actuation, including electromagnetic, electrorheological, magnetorheological, and magnetic particle clutch types.

In some embodiments, the operation of the wrist rotation joint 114 and the elbow joint 100 can be separate. In some configurations, a different release control can be provided for each joint. In other configurations, the wrist rotation joint 114 can be passively repositionable, i.e., not directly coupled to the locking and unlocking of the elbow joint and rotatable with the application of sufficient force using the paretic arm.

In still other embodiments, the degree to which a joint is locked can vary. For example, the user may have diminished strength in the paretic arm and can utilize the orthotic device to stabilize this arm. However, for certain tasks, the user may not wish to have his elbow and wrist joints completely locked in place. Accordingly, in some configurations, the clutch/brake mechanism for joints 110 and 114 can be configured to allow some play. Further, in other configurations, the clutch/brake mechanism for joints 110 and 114 can be configured to allow motion when sufficient strength is applied by the user. For such alternative embodiments, the orthotic device 100 can be configured to allow such play as a default or can provide one or more additional controls (not shown) on orthotic device 100 to allow the user to adjust the amount of play as needed.

Figure 2A:
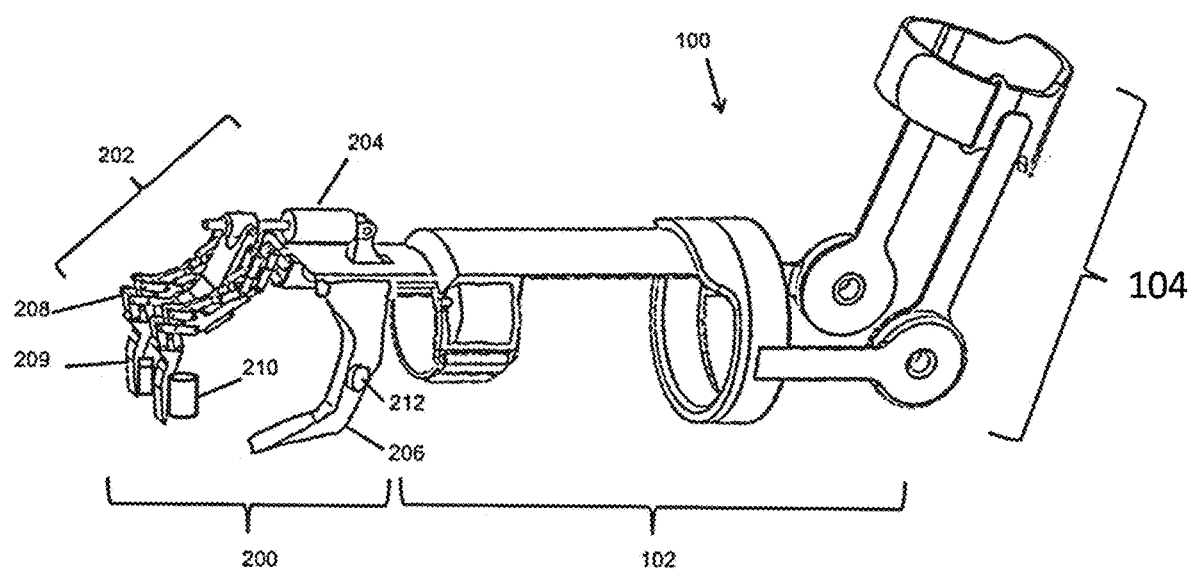
FIGS. 2A-2B show the exemplary orthotic device of FIG. 1, outfitted with a hand portion useful for discussing various embodiments.

In some configurations, the orthotic device 100 can include a hand portion 200 attached to a distal end of forearm portion 102. This is illustrated in FIG. 2A. The hand portion 200 can include first portions that actively assist with the opening and closing of the digits of the paretic arm and which can be combined with second portions that provide passive support. The first portions that assist with movement can include an actuator to provide active (or powered) movement assistance.

For example, as illustrated in FIG. 2A, the hand portion 200 can include a hand movement assistance component 202 that provides active movement assistance to the fingers via an actuator 204 (e.g., an electric motor, or pneumatic or hydraulic actuator). Other components, such as batteries and the like are not shown for ease of illustration and discussion. The hand portion can also include a passive component 206 that supports the thumb in a semi-rigid manner and enables the thumb of the paretic arm to resist grasp forces during grasp. In order for the movement assistance component 202 to reside on the posterior aspect of the digits, the design should employ a remote center mechanism, such as the remote center linkage 208 operatively coupling rigid digits 209 to the rest of hand portion 200, as shown in FIG. 2A. Optionally, the rigid digits 209 can include digit securing elements 210 to facilitate manipulation of the digits. Finally, in order to cause repositioning of the hand of the paretic arm (e.g., open or close the hand), the hand portion 200 can include a button, switch, or control 212 for the hand 200. In some configurations, the hand control 212 can be a toggle switch which can toggle the hand 200 between an open and closed configuration or between any other two or more configurations. Alternatively, hand control 212 can be a lever or rotary switch to allow the hand 200 to alternate between two or more postures. In still other configurations, multiple controls can be provided, where the activated combination of controls can determine the configuration of hand 200 required by user.

In the actuator-assisted embodiment, a powered actuator, such as an electric motor, can be used to assist with the opening or closing of the hand. In the actuated hand portion embodiment, the hand can be toggled between the open and closed configurations with a button or switch located on the hand portion. The button or switch that toggles between the open and closed configurations of the paretic hand can be situated on the thumb. In one embodiment, the thumb portion of the hand orthotic device can be passive, such that the thumb is essentially maintained in a neutral posture, such that only the finger digits are actuated and configured to open or close.

In some cases, the closing of hand 200 can be commanded when a deflection of the digits in the opening direction is detected, for example by a strain sensor or compliant motion sensor associated with the digits. Alternatively, a contact sensor or button on the anterior aspect of the digits could be employed. Similarly, opening of hand 200 can be commanded when a deflection of the digits in the closing direction is detected, such as by a strain sensor or compliant motion sensor, or by a contact sensor or button on the posterior aspect of the digits, or when the button 212 is used to release the grasp. For example, the hand can open or close based on detection of a change in position or force on the digits, such as would be imposed by the non-paretic arm. In one embodiment, if the hand is in the open configuration a movement or force is detected further opening the hand, the hand will move to the closed configuration. In the closed configuration, if movement or force further closing the hand is detected, the hand will move to the open configuration. With this approach, the hand will close around an object when an object is pushed into the hand (such as by the non-paretic arm), deflecting the digits accordingly. Conversely, an object can be released by pushing against posterior aspect of the digits while grasping an object, thus causing the hand to open. In this manner, disturbances that tend to open the hand while grasping an object will not cause accidental release of the object. In another embodiment, the hand open and close is conveyed by a combination of detecting movement or force, and using a button. For example, the hand closing can be initiated by detection of digit opening, while hand opening can be initiated by pressing release control 212 on the hand portion 200.

In some configurations, the configuration of hand portion 200 can vary based on the number and types of postures required for the hand of the paretic arm. In a configuration where the hand is alternated between open and closed positions, a single actuator 204 can be provided, as shown in FIG. 2A, that operates the joints of the hand 208 so that the hand and all digits act in concert. In other configurations, multiple actuators can be provided for different parts of the hand. Thus, the hand portion 200 can be utilized to configure the hand in a variety of postures, including controlling each of the digits of the hand separately.

Figure 2B:
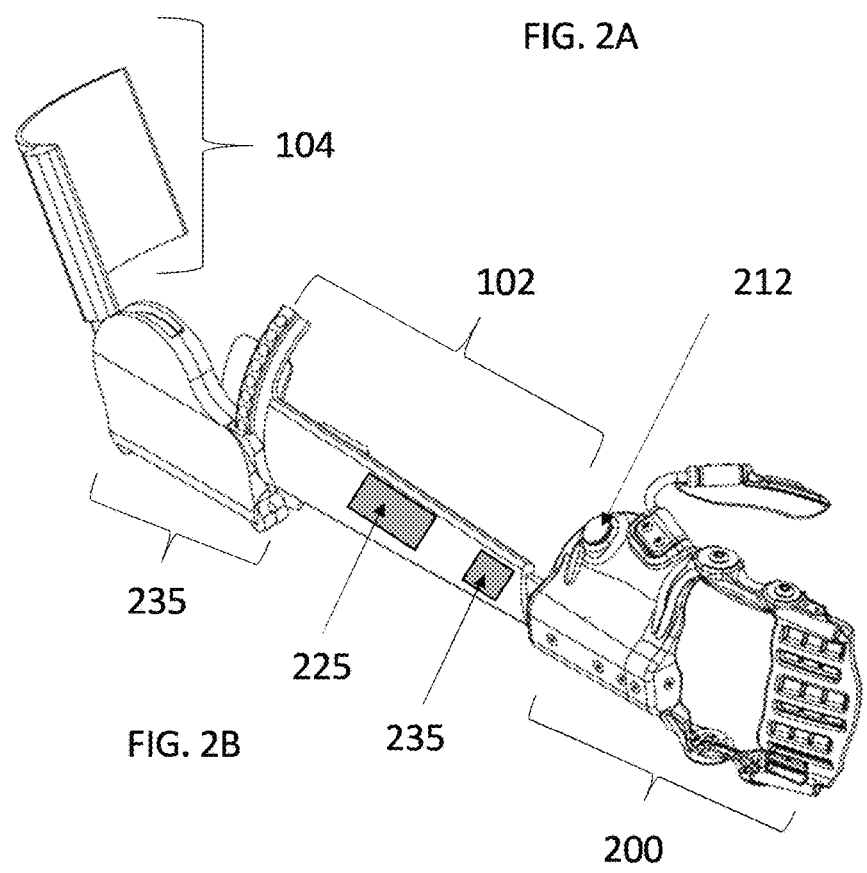

In one embodiment, such control functionality can be provided via a controller 225 as shown in FIG. 2B. The controller 225 can receive input signals from a hand control 212 and generate control signals for the powered hand portion 200 according to the input signals received from the hand control 212. The controller 225 can also send input to an indicator 235. The indicator 235 can be a light or provide audible or tactile alerts to provide feedback to the user regarding control action of the orthotic device. The controller 225 and the indicator 235 can be found on the forearm portion 102. The controller 225 and the indicator 235 can also be placed anywhere on the orthotic device without limitation.

The hand control 212 can be various types of an electrical switch, or switching element. In one embodiment, the hand control 212 is a momentary electrical switch, where momentary activation of the switch toggles the hand between the open configuration and the closed configuration. In an exemplary embodiment, momentary activation of the hand control toggles the hand between the open configuration and the closed configuration following a predetermined time delay (e.g., a 2-seconds delay). The hand control can be located on the hand portion of the orthotic device, or any other location of the orthotic device without limitation. Further, the various embodiments are not limited to any particular time delay.

In an exemplary embodiment, the controller 225 can generate the control signals following a predetermined time delay, wherein the predetermined time delay is initiated upon release of the momentary switch. In this embodiment, when the hand is in the open configuration, the delay allows a user to use his or her unaffected hand to depress the hand activation switch, then allows sufficient time to use the same unaffected hand to place an object in the affected hand before the hand movement assistance device (and affected hand) closes around the object to be held. Similarly, when the hand is grasping an object in the closed configuration, the time delay following switch release allows a user to use his or her unaffected hand to depress the hand activation switch, then use the same unaffected hand to grasp or secure the held object held in the affected hand before it is released by the hand movement assistance device. As such, the time-delayed action is an enabling feature that allows the user to use the same unaffected hand to both command action of the affected hand, and to place or remove objects from the affected hand. The controller 225 can be configured to reset the predetermined time delay after any subsequent activation of the hand control 212.

In response to additional input signals from the hand control 212, the controller 225 can configure the control signals to cause the powered hand portion to alternate between the open position and the closed position. The amount of force used to alternate between the open position and the closed position can be proportional to a number of the one or more second temporary activations of the hand control 212.

In certain embodiments, it is also desirable to control the amount of grasping force applied by the hand movement assistance device. Specifically, a large grasping force may be desirable for taking the lid off of a bottle or jar, while a smaller grasping force may be desirable for holding a delicate object. Control of grasp force can be afforded in the momentary switch exemplary embodiment by using a successive momentary activation of the hand control within the period of time delay (i.e., between the time the hand control is momentarily activated and the time the hand moves) to increase the commanded hand closing (or opening) force.

For example, consider the case where the predetermined time delay is 2 seconds, the nominal hand closing force is 30 N, and the closing force increment is 5 N. In such a configuration, when the hand is in the open configuration, a single momentary activation (i.e., depression) of the hand control will result in the hand closing with a grasp force of 30 N, where the closing movement of the hand will begin 2 seconds after the hand control is released. If within the 2-seconds time delay period, the hand control is again momentarily activated, the hand will close with a grasp force of 35 N (30+5 N) rather than 30 N, with the closing movement commencing 2 seconds after the release of the last activation. If the hand control is depressed 3 times following the initial momentary activation, each within 2 seconds of the previous release, the hand will close with a closing force of 45 N (30+5+5+5 N), with movement commencing 2 seconds after the release of the last activation. The same procedure can be used to control the amount of opening force, in the case that the hand starts in the closed configuration. However, the various embodiments are not limited to any particular force or increment of force. Rather, the amounts and increments of force can vary amount the various embodiments. In some embodiments, the increments even need not be the same. For example, the increments for increasing the grasp force can decrease with each additional activation. Thus, the increases in grasp force with each additional activation can be linear or non-linear.

In certain embodiments, an alternate mode of hand operation may be desirable. In a preferred alternate mode of operation, rather than be used to perform activities of daily living, the hand movement assistance device may be used to gently and repetitively open and close the hand, which may have musculoskeletal therapeutic benefit to the individual. In the same momentary switch embodiment, continuous depression of the momentary switch for a predetermined period of time (e.g., 5 seconds) can cause the controller 225 to operate the powered hand using such an alternate control mode. For example, the alternate control mode can cause the powered hand to continuously cycle between the open position and closed position for a predetermined number of cycles.

In one exemplary embodiment, the alternate mode is a therapeutic mode, where the hand assistance component 202 cycles repeatedly between the hand open and hand closed configurations for a predetermined number of cycles (e.g., 120 cycles) or predetermined period of time (e.g., 10 min). Following the predetermined number of cycles or period of time, the hand can revert to the default control mode (i.e., toggle between open and closed). Alternatively, continuous depression of the momentary switch for the predetermined period of time (e.g., 5 seconds) can toggle the hand to the default control mode. For the same momentary switch embodiment, continuous depression of the momentary switch for a longer predetermined period of time (e.g., 10 seconds) can cause the controller 225 to power off the device. A state chart of a set of possible embodiments for the momentary switch is discussed further with respect to FIG. 8A. However, the various embodiments are not limited to any particular time period.

In another embodiment, hand control 212 is an electrical toggle switch, where the toggle switch can be configured into at least a first switch position for causing a first configuration of input signals. The toggle switch can also be configured in a second switch position for causing a second configuration of the input signals. In response to the input signals being in the first configuration, the controller configures the control signals to cause the powered hand portion to transition towards the closed position. In response to the input signals being in the second configuration, the controller can configure the control signals to cause the powered hand to transition towards the open position. In an exemplary embodiment, movement of the hand commences following a predetermined time delay following the configuring of the toggle switch into the first or second positions.

In another exemplary embodiment, the electrical toggle switch is a three-position toggle switch, where the third position is a normally-off neutral position, where the neutral position is located between the first switch position and the second switch position. In this embodiment, the switch is configured into either the first or second switch positions in a momentary manner, and when not held in the first or second position, the switch returns to the neutral position. Momentarily configuring the toggle switch into the first switch position configures the hand in the closed configuration, where movement of the hand commences following a predetermined time delay following release of the switch. Momentarily configuring the toggle switch into the second switch position configures the hand in the open configuration, where movement of the hand commences following a predetermined time delay following release of the switch. In this embodiment, for a 2-seconds time delay, when the hand is in the open configuration, momentarily configuring the switch to the first position will cause the hand to close 2 seconds following release of the switch. However, the various embodiments are not limited to any particular time delay.

This time delay enables a user to use his or her unaffected hand to command the hand to close, and allows him or her time to use the same unaffected hand to place the object to be held in the affected hand. If grasping an object, configuring the toggle switch momentarily into the second position will cause the hand to open 2 seconds following release of the switch. This time delay enables a user to use his or her unaffected hand to command the hand to open, and allows him or her time to subsequently use the same unaffected hand to grasp the object prior to it being released. As such, the time-delayed action allows the user to use the same (single) unaffected hand to both command action of the affected hand, and to place or remove objects from the affected hand.

Considering the same three-position toggle switch, the controller can configure the control signals so that the magnitude of force used for closing or opening the hand can be commanded either as a function of how long the switch is maintained away from a neutral position, or by the number of successive activations. For example, if the hand is closed, the controller can increment the amount of grasping force by successive activations of the toggle switch into the first position. If the hand is open, the controller can decrement the amount of closing force by successive activations of the toggle switch into the second position.

Similarly, if the hand is closed, the amount of grasping force can be decreased incrementally by successive activations of the toggle switch into the second position. In this embodiment, when the hand is closed, a brief momentary activation of the switch into the second position will decrement the force, while a somewhat more sustained activation will initiate opening of the hand, following a predetermined time delay. This configuration enables a user to increase or decrease grasping force while grasping an object. For example, consider the case where the time delay is 2 seconds, the nominal grasp force is 30 N, and the grasp force increment is 5 N. If the hand starts in the open configuration, momentary activation of the switch into the first position will command the hand to close with a grasp force of 30 N, 2 seconds following release of the switch. Once the hand has grasped the object, each successive momentary activation of the switch into the first position will increment the grasp force by 5 N. Each successive momentary activation of the switch into the second position will decrease the grasp force by 5 N. As previously discussed, the various embodiments are not limited to any particular force or increment of force. Rather, the amounts and increments of force can vary amount the various embodiments. In some embodiments, the increments even need not be the same. For example, the increments for decreasing the grasp force can increase with each additional activation. Thus, the increases in grasp force with each additional activation can be linear or non-linear.

In an exemplary embodiment, the grasp force will have an upper and lower bound. In the closed configuration, a longer momentary activation of the switch into the second position will command opening of the hand (i.e., 2 seconds after release of the switch). In this embodiment, if a user is attempting to remove the lid from ajar being grasped, and if the jar is slipping rotationally with the affected hand, the user can incrementally increase the grasp force until the force is sufficient to preclude slipping. If instead the grasp force is too high and a delicate object is being deformed, the user can decrease the grasp force accordingly.

For the same embodiment, continuous activation of the momentary switch into either position for a predetermined period of time (e.g., 5 seconds) can toggle to an alternate control mode, rather than toggle the hand between the open and closed configurations. For example, in response to the powered hand portion being in the open position and the input signals indicating a continuous activation of the toggle switch in the second switch position for a first period of time, the controller can configure the control signals to switch the controller to operate the powered hand portion using the alternate control mode. In another example, the controller can configure the control signals to switch the controller to operate the powered hand portion using the alternate control mode when the powered hand portion is in the closed position and input signals indicate a continuous activation of the toggle switch in the first switch position for the first period of time. In an exemplary embodiment, this toggle to an alternate mode can occur only from the open hand configuration via a continuous activation of the switch in the second position. In this manner, the hand must be open to switch into the alternate mode, such that an object will not be accidentally or inadvertently dropped.

In one exemplary embodiment, the alternate mode is a therapeutic mode, where the hand assistance component 202 cycles repeatedly between the hand open and hand closed configurations for a predetermined number of cycles (e.g., 120 cycles) or predetermined period of time (e.g., 10 min). Following the predetermined number of cycles or amount of time, the hand can revert to the default control mode. For example, continuous depression of the momentary switch for the predetermined period of time (e.g., 5 seconds) can toggle the hand back to the open configuration and the default control mode of operation.

In another exemplary embodiment, the controller can be configured to power off the device. For example, when the hand is in the open configuration, continuous activation of the momentary switch into the second position for a longer predetermined period of time (e.g., 10 seconds) can power off the device. When the hand is in the closed position, continuous activation of the momentary switch into the first position for a predetermined period of time can power off the device.

Transitions between the open and closed positions and transitions into an alternate control mode or a powered off state can be provided via a state chart. A state chart of an exemplary control structure is discussed further with respect to FIG. 8B. However, the various embodiments are not limited to any particular time periods.

In another embodiment of the three-position toggle switch control, the magnitude of force can be increased or decreased in relation to the length of time the toggle switch is held in either the first or second position, rather than in relation to the number of times the toggle switch is successively activated. If the toggle switch is held into the respective position prior to movement, the time delay can start when the switch is released, and the force of movement is programmed by the duration of time the switch was held. If the toggle switch is held into the respective position following movement, the force is incremented or decremented in relation to the length of time held. In an exemplary embodiment, the grasp force will have an upper and lower bound.

Various elements of FIG. 2B are optional for various embodiments of the present disclosure. For example, an elbow joint 235 or an upper arm portion 105 are not needed. In the various embodiments, the orthotic device can optionally be mated to a shoulder assistance portion. The shoulder assistance portion can be configured to support the orthotic device of the various embodiments. In some configurations, the shoulder assistance portion can also be configured to operate cooperatively or independently of orthotic device to allow a user to reposition an arm with respect to the shoulder joint.

Figure 3:
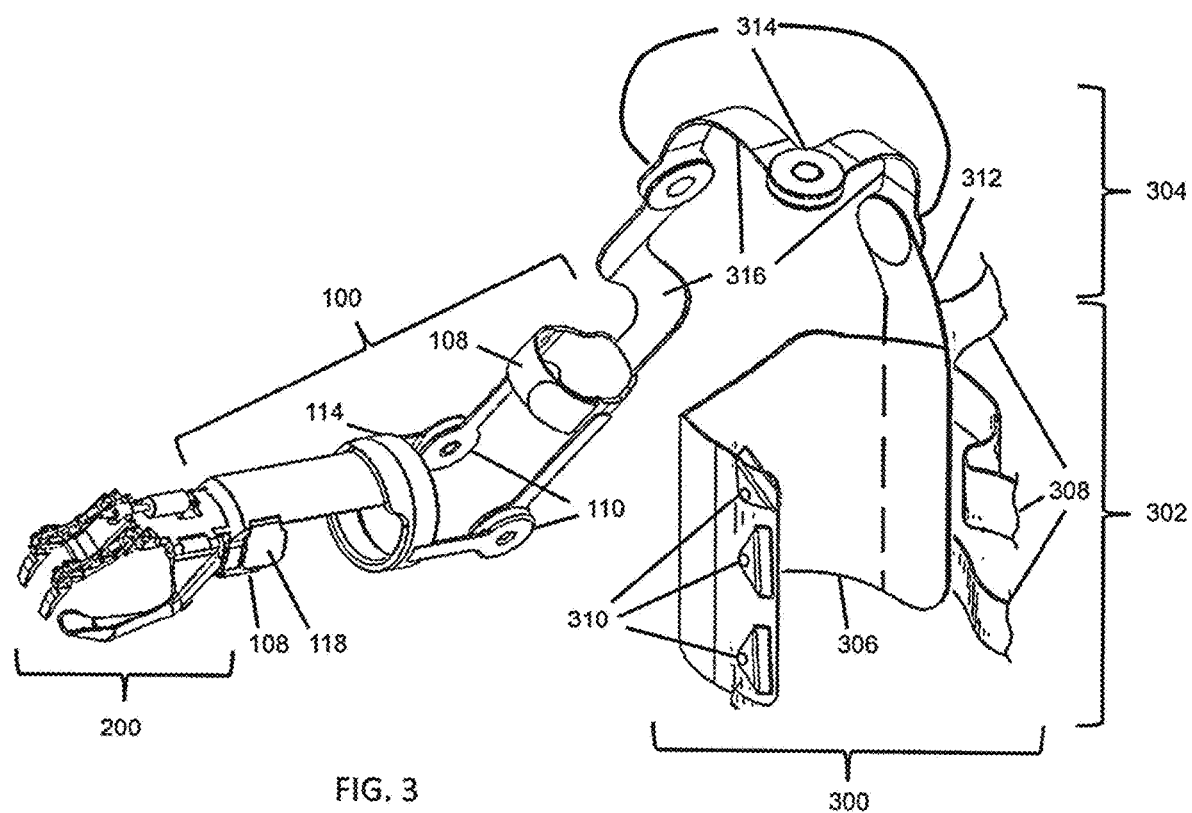
FIG. 3 shows the arrangement of FIG. 2A mated to a shoulder control portion.

An orthotic device in accordance with the various embodiments can also include features for controlling a shoulder joint. One exemplary configuration for providing such control is illustrated with respect to FIG. 3. FIG. 3 shows an exemplary configuration for adapting orthotic device 100 to provide manipulation of a shoulder joint. In particular, FIG. 3 shows that orthotic device 100 can be mated with a shoulder control portion 300 including a base section 302 and a shoulder orthosis 304

The base section 302 is configured for attachment to a trunk of a user. As shown in FIG. 3, the base section 302 thus includes a cuff 306 that engages with the trunk of a user. To hold the cuff 306 in place, straps 308 are provided that extend from one side of cuff 306 to wrap over an opposite shoulder of the user and the trunk of the user and engage with retaining elements 310 on another side of cuff 306 to hold cuff 306 in place. The cuff 306 can include rigid or resilient portions to support mounting of elements thereon (e.g., shoulder orthosis 304, as described below) and interior padded portions (not shown) to provide comfort for the user.

The shoulder orthosis 304 can include a support member 312 attached to the cuff 306. The form of attachment is selected to support the weight of the shoulder orthosis 304, orthotic device 100, and (if present) hand portion 200. In general, the support member 312 can be slidably attached or otherwise be repositionable in order to allow adjustment of the position of shoulder control portion 300 and orthotic device 100 to accommodate anatomical differences between different users.

As shown in FIG. 3, at a distal end of the support member 312 a one or more shoulder joints 314 can be provided to allow motion of the paretic arm. As shown in FIG. 3, the shoulder orthosis 304 includes three joints corresponding to the three degrees of freedom In an intact shoulder (internal/external rotation, flexion/extension, and abduction/adduction). The joints 314 can be mechanically coupled to each other, to support member 312, and to orthotic device by structural portions 320 to attach orthotic device 100 thereto. In the various embodiments, the structural portions 320 can be configured to be adjustable or otherwise be repositionable in order to allow repositioning of the joints 314 with respect to the orthotic device 100 or the structural member 312 to accommodate anatomical differences between for different users.

In some embodiments, the shoulder rotation joints 314 can be normally locked, similar to elbow joint 110 and wrist rotation joint 114. Thus, joints 314 can also include clutch or brake mechanisms, as previously described with respect to FIG. 1. Further, release control 118 can also be configured to operate with joints 314 in shoulder orthosis 304. That is, upon grasping and squeezing the portion of the securing element 108 including the release control 118, near the anatomical wrist joint of the paretic limb, the shoulder orthosis 304 is also configured so that the shoulder joints 314, the elbow joint 110 and the wrist joint 104 are contemporaneously unlocked. Similar to joints 110 and 114, the release control 118 can be operationally coupled to joints 314 via mechanical or electrical means. While unlocked, a user can then reposition the paretic arm, with respect to their shoulder joint, using their non-paretic arm. Once the release control 118 is released by user, the clutch mechanisms in joints 314 are reactivated and the paretic arm is locked into the new pose.

In some configurations, the release control 118 can be limited with respect to the joints it operates (i.e., the clutch/brake mechanisms it releases). For example, in some configurations, the release control 118 can be limited to operating the elbow joint 110 and the wrist rotation joint 114 and a separate release control (not shown) can be provided for shoulder joints 314. This separate control can be located in the vicinity of release control 118 or elsewhere. For example, the separate control (not shown) can be located with securing element 108 in the upper arm portion 104 of orthotic device 100, to allow the user to grasp and reposition in a similar fashion as with release control 118.

Although FIGS. 1-3 show specific configurations for hand portion 200, orthotic device 100, and shoulder control portion 300, the present technology is not limited in this regard. In particular, the number and types of components shown for each of these in FIGS. 1-3 is solely for purposes of illustration. In other embodiments, the number and types of components can vary.

Figure 4A:
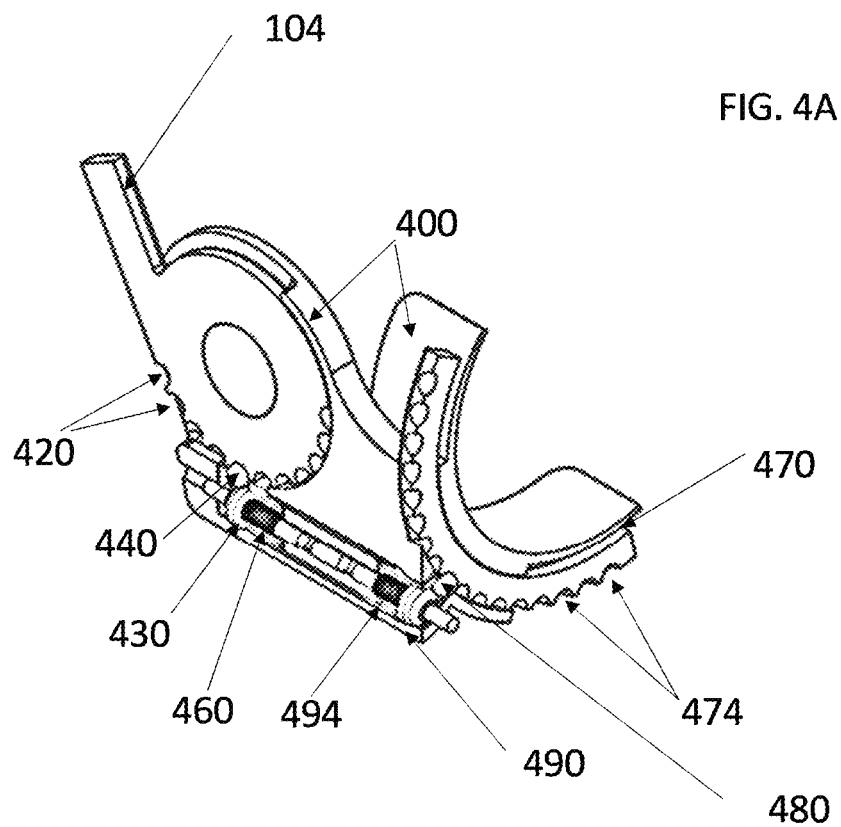
FIGS. 4A-4B show a schematic diagram of an exemplary embodiment of an electrically-actuated clutch according to the present disclosure.
Figure 4B:
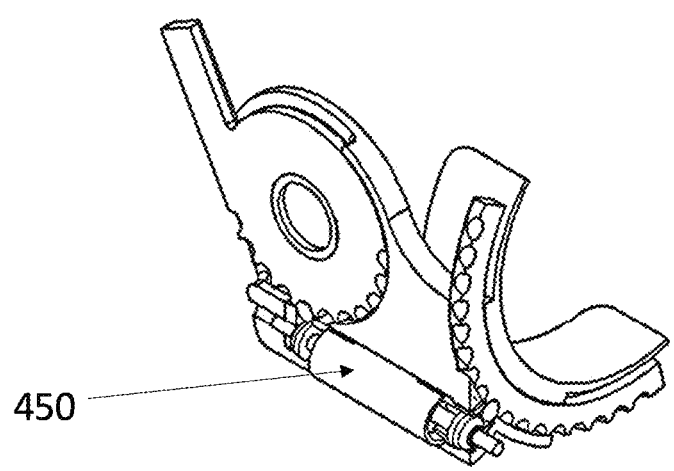

An exemplary embodiment of an electrically-actuated normally-locked elbow joint is shown in FIGS. 4A and 4B. FIG. 4A shows a clutch disc 410 affixed to the upper arm portion 104. The clutch disc 410 is constrained to rotate within an elbow housing 400. The clutch disc 410 contains a series of detents 420, generally spaced at regular intervals around at least a portion of the clutch disc. In an exemplary embodiment, the detents are located on the radial surface of the clutch disc. A sliding member 430 is also contained within the elbow housing 400, and can be slidably configured between a first slider position and a second slider position. When configured in the first slider position, the sliding member 430 traps a bearing element 440 between the sliding member 430, the elbow housing 400, and the detent 420 within the clutch disc 410, thus rotationally locking the clutch disc relative to the elbow housing. When configured in the second slider position, the sliding member 430 moves such that a reduced-diameter portion of the slider is in contact with the bearing element, which effectively releases the bearing element 440 from the detent in the clutch disk, thus rotationally unlocking the clutch disc relative to the elbow housing. In an exemplary embodiment, the sliding member is maintained in the first slider position by a return spring 460.

FIG. 4B shows how a solenoid actuator 450 can be used to pull the sliding member 430 into a solenoid actuator, and thus configure the sliding member into the second slider position. As such, energizing the solenoid actuator unlocks the elbow joint, while de-energizing the solenoid actuator returns it to a locked state.

The embodiments shown in FIG. 4A and FIG. 4B can be used in the device of FIG. 3. For example, in one exemplary embodiment of the orthotic device 100, the elbow housing is affixed to a forearm portion 102. The release lever, button, or control 118 is configured to energize solenoid actuator 450, in which case the solenoid will configure the sliding member 430 into the second slider position, which unlocks the clutch disc 410 and associated upper arm section 104 from the elbow housing 400 and associated forearm portion 102, and thus will allow elbow repositioning. When the release control 118 is released, solenoid 450 is de-energized, and the return spring 460 returns the sliding member 430 to the first slider position, which locks the clutch disc relative to the elbow section, and therefore locks the elbow joint. As such, the elbow joint is normally locked, but is released to be repositioned when the release control 118 is engaged.

Figure 4C:
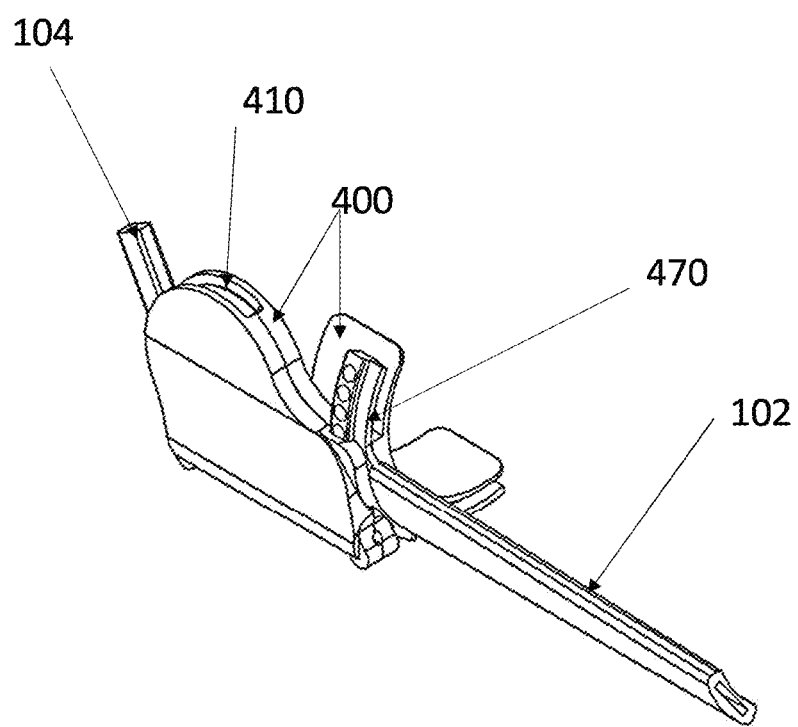
FIG. 4C shows a schematic diagram of an exemplary electrically-actuated wrist clutch according to an embodiment of the present disclosure.

In another exemplary embodiment, the orthotic device 100 contains an electrically-actuated elbow and wrist rotation clutch. In this embodiment, the elbow housing 400 contains the elbow clutch mechanism 410, 420, 430, 440, 450, and 460, as previously described, and additionally contains a wrist clutch mechanism for locking and unlocking of wrist rotation. An exemplary wrist clutch mechanism schematic diagram is shown in FIG. 4C. Construction of an orthotic mechanism that can lock and unlock wrist rotation is a challenge, notably because (unlike some other joints in the human body, such as the elbow joint) the axis of wrist rotation is aligned axially with the anatomical forearm, and as such is not easily accessible to an external arm orthosis.

A basic elbow clutch mechanism can include at least one rotating member, at least one sliding member, and at least one bearing member. The at least one rotating member can include at least one detent and can be affixed to a first arm section. The at least one sliding member can slide through a second arm section such that the at least one rotating member rotates relative to the at least one sliding member. The at least one detent can be on a radial aspect of the at least one rotating member and can be cylindrical or spherical in shape.

Various remote center mechanisms (see for example, the remote-center linkages used in the hand device in FIG. 2A to accommodate finger movement) can be used to accommodate wrist rotation from an external orthosis, but such remote-center mechanisms that can lock movement against the required loads are generally complex, bulky, and heavy. An arm orthosis such as the device described here must be compact and lightweight to be an effective assistive device. Further, remote-center mechanisms typically incorporate multiple links and joints to accommodate a single remote axis of rotation, and the existence of multiple joints can substantially increase the complexity of locking and unlocking device motion. The normally-locked wrist rotation clutch embodiment described here provides a lightweight and compact means of locking and unlocking the wrist rotation axis of motion, as required by the arm orthosis described here. Additionally, the embodiment provides this function without encircling the forearm, which greatly facilitates donning and doffing of the arm orthosis. The embodiment also facilitates a normally-locked device that can be unlocked using a common mechanism to simultaneously unlock the elbow and wrist joint.

FIG. 4C shows how the wrist clutch mechanism includes a constant-radius curvilinear sliding member 470 that slides within elbow housing 400. In an exemplary embodiment, curvilinear sliding member 470 is configured such that its axis of rotation is coincident with the nominal anatomical axis of wrist rotation. In this exemplary embodiment, the curvilinear sliding member 470 is affixed to the forearm portion 102 of the orthotic device 100, and is constrained to slide within the elbow housing 400. The curvilinear sliding member 470 contains a series of detents 474, generally spaced at regular intervals around at least a portion of sliding member 470. In an exemplary embodiment, the detents are located on the radial surface of the clutch disc. The wrist clutch mechanism further comprises a sliding member 490, also contained within the elbow housing 400, which can be slidably configured between a first slider position and a second slider position. When configured in the first slider position, the sliding member 490 traps a bearing element 480 between the sliding member 490, the elbow housing 400, and the detent 474 within the curvilinear sliding member 470, thus rotationally locking the curvilinear sliding member relative to the elbow housing. When configured in the second slider position, the sliding member 490 moves such that a reduced-diameter portion of the sliding member is in contact with the bearing element, which effectively releases the bearing element 480 from the detent in the curvilinear sliding member, thus unlocking the curvilinear sliding member relative to the elbow housing.

In an exemplary embodiment, the sliding member 490 is maintained in the first slider position by a return spring 494. In the same exemplary embodiment, a solenoid actuator 450 is used to pull the sliding member 490 into the solenoid actuator, and thus configure the sliding member into the second slider position. As such, energizing the solenoid actuator unlocks the wrist joint, while de-energizing the solenoid actuator returns it to a locked state. In this configuration, the solenoid need only be energized to unlock the joints, which minimizes electrical power consumption, and thus minimizes battery requirements. Although two separate solenoid actuators could be used to unlock the respective normally-locked clutch mechanisms, In an exemplary embodiment, both sliding members 430 and 490 are pulled in by the same solenoid actuator. It should be noted that, in this embodiment, although the sliding members 430 and 490 are both pulled in by the same solenoid, the two sliding members can move independently of each other. In this manner, although both joints will unlock simultaneously, one is not dependent on the other in order to return to a locked state. For example, in some instances, one of the two joints may not be immediately aligned with a corresponding detent, while the other is aligned. In such a case, the aligned joint will lock immediately, while the misaligned joint will lock as soon as external loads adjust the alignment to allow locking. Note that, in the absence of external loads, the locking function serves no purpose. As such, requiring external loads to facilitate locking does not limit functionality.

In some embodiments, the elbow clutch mechanism can be a friction clutch, a dog clutch, a wrapped spring clutch, or a belt clutch type. The electrically-actuated clutch can be of the electromagnetic, electrorheological, magnetorheological, or magnetic particle types. However, the various embodiments are not limited to any particular clutch mechanism. Thus, other clutch mechanisms, other than those listed above, can be used without limitation.

Figure 5:
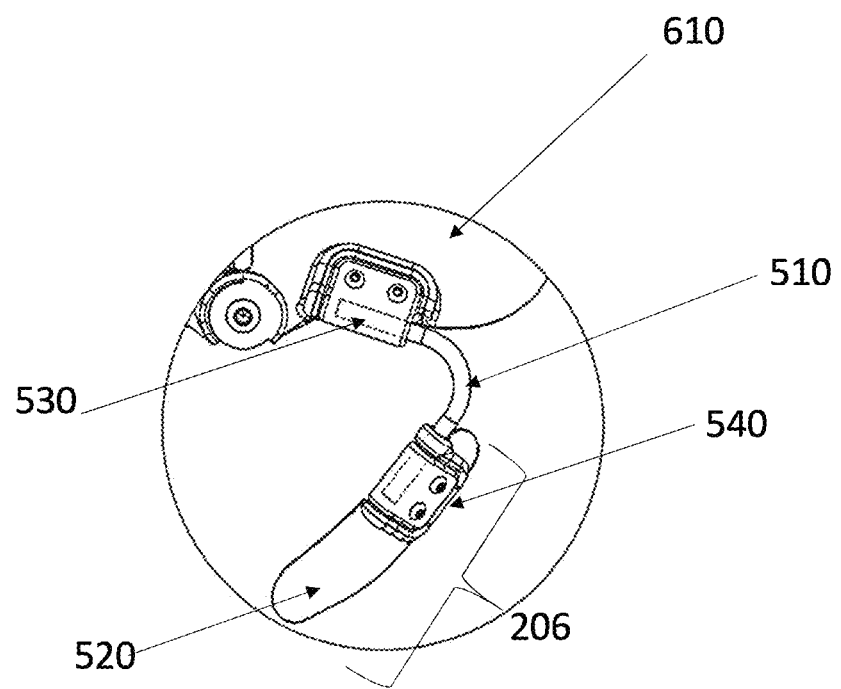
FIG. 5 shows a schematic diagram of an exemplary thumb component according to an embodiment of the present disclosure.

The hand portion 200 can accommodate a large range of hand sizes and shapes. One aspect of human hand geometry that can vary considerably is the size, position, and orientation of the thumb relative to the palm and fingers. A viable hand portion should therefore enable accommodation of thumb position in a compact, lightweight, effective, and minimal cost manner. FIG. 5 shows an exemplary embodiment of thumb component 206 that enables a large range of passive adjustment of thumb geometry. The passive thumb component consists of a thumb rod 510 and thumb cup 520, wherein the thumb rod connects the thumb cup to the hand portion via a hand portion clamping joint 530 and thumb cup clamping joint 540, where the clamping joints 530 and 540 allow rotational and translational adjustment of the thumb rod when loosened. In another exemplary embodiment, the hand portion clamping joint 530 can be replaced with a frictional or ball-detent joint, such that rotation or translation of the thumb rod relative to the hand portion can be achieved without requiring a loosening of the clamp. In this embodiment, the thumb can be passively repositioned, presumably by the unaffected hand, between two or more positions. For example, the thumb could be manually positioned in opposition (i.e., palmar adduction) for certain grasps (such as grasping a bottle), or could be manually re-positioned in reposition (i.e., palmar abduction) for other grasps (such as grasping a handle).

In a general embodiment, the orthotic device can include distal linkages and at least one digit-securing element. The digit-securing element can be comprised of at least a strapping element and a quick-connect base element. The quick-connect base element can be comprised of a convex surface configured for snapping into a mating set of receiving clips of the distal linkage.

The hand movement assistance component 202 should be compact and lightweight, such that it minimally interferes with hand use. The hand movement assistance component 202 should also ideally allow conformable grasping. Conformal grasping enables grasping of variable shapes, such as spherical, conical, or arbitrary shapes. Conformal grasping requires that the fingers on the medial and lateral sides of the hand move semi-independently, and as such can close around variable shapes, thus making conformal contact and providing a stable grasp. In the case that a gradient of movement does not exist between the medial and lateral digits, the hand will generally make a line or point contact with an object, and the grasp may be considerably less stable, causing the object to fall or slide out of the hand. As such, an important objective of an effective hand design for providing stable grasping is to allow a gradient of movement between the medial and lateral aspects of the hand when grasping an object.

Figure 6A:
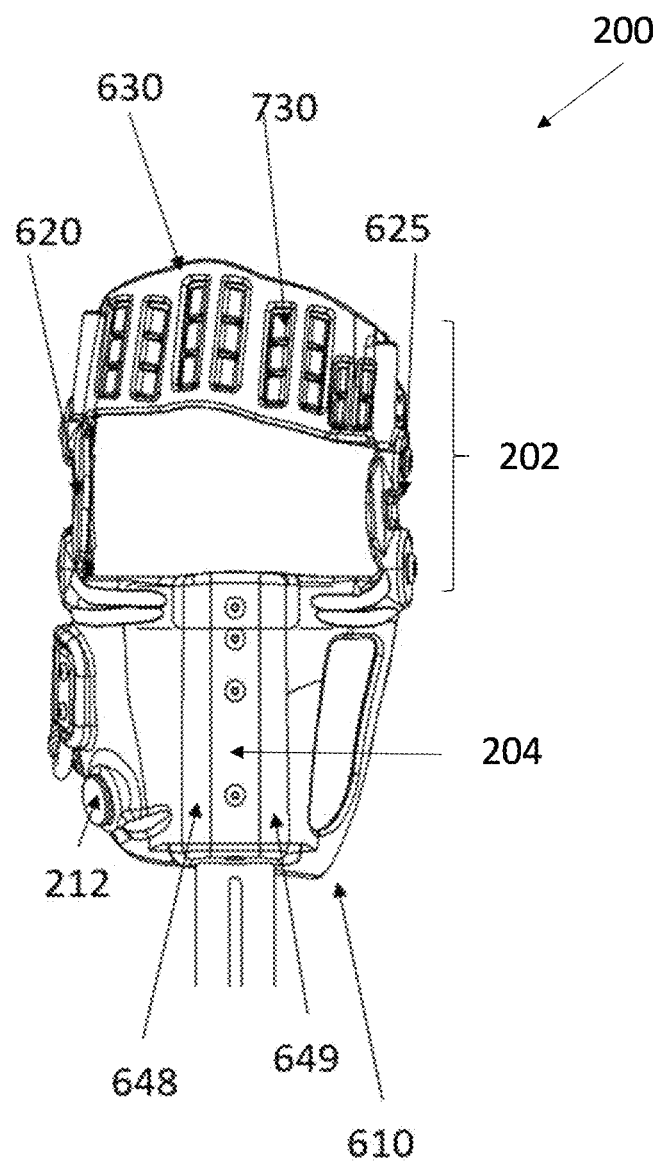
FIG. 6A-6C show a schematic diagrams of exemplary linkages of a hand movement assistance device according to an embodiment of the present disclosure.
Figure 6B:
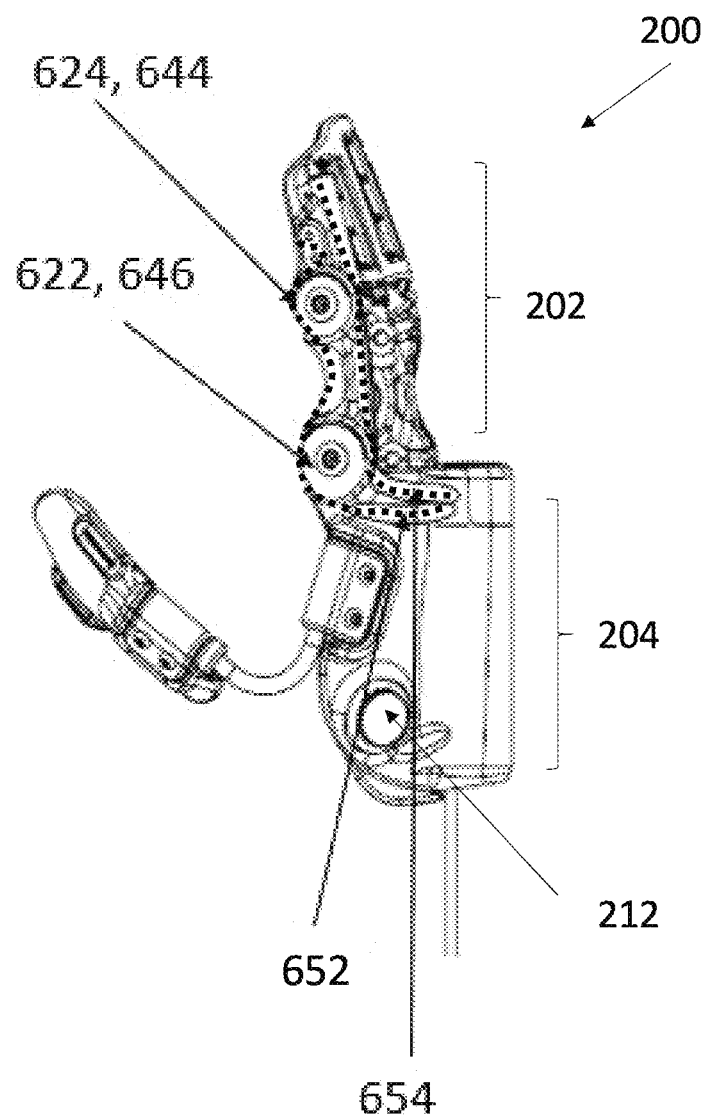
Figure 6C:
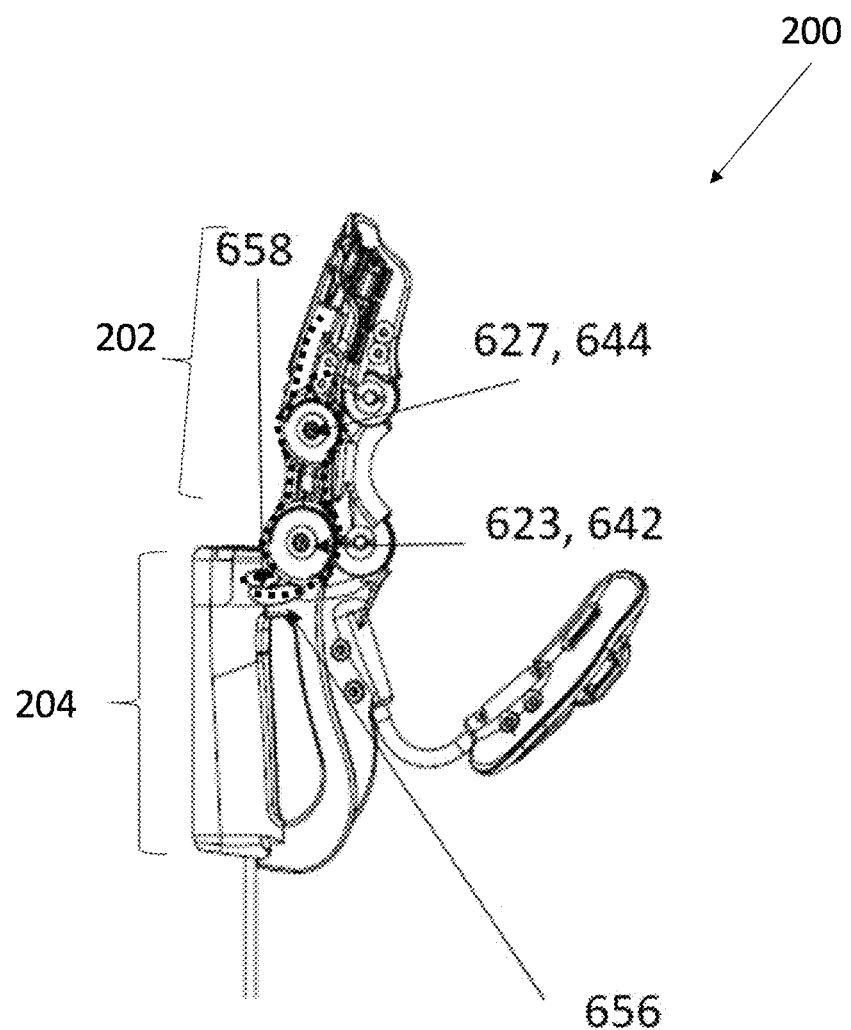

FIG. 6A-6C show exemplary embodiments of a hand movement assistance component 202 that provides active movement assistance to the fingers via actuator 204, and enables a gradient of movement between the medial and lateral digits, thus facilitating conformal grasp. The orthotic device can comprise a forearm section and a powered hand portion coupled to a distal end of the forearm section. The powered hand portion can be comprised of a plurality of linkages and at least one powered actuator to assist with an opening and closing of the hand portion. The plurality of linkages can comprise linkages configured to adjoin to portions of a subject's hand. FIG. 6A provides a front view of an exemplary embodiment while FIGS. 6B and 6C provide side views.

In an exemplary embodiment, the hand portion 200 (excluding thumb) is comprised of four essential linkages, including a metacarpal base linkage 610; a distal phalange linkage 630; and lateral and medial connecting linkages, 620 and 625. A first end of the lateral connecting linkage 620 is rotatably connected to the metacarpal base linkage 610 via a rotational joint 622, which has an axis of rotation coincident with the nominal axis of rotation of the metacarpal phalangeal joints 642 of the anatomical hand. A second end of the lateral connecting linkage 620 is rotatably connected to the distal phalange linkage 630 via a rotational joint 624, which has an axis of rotation coincident with the nominal axis of rotation of the proximal interphalangeal joints 644 of the anatomical hand. Independently of lateral connecting linkage 620, a medial connecting linkage 625 is rotatably connected to the metacarpal base linkage 610 via a rotational joint 623, which has an axis of rotation coincident with the nominal axis of rotation of the metacarpal phalangeal joints 642 of the anatomical hand. A second end of the medial connecting linkage 625 is rotatably connected to the distal phalange linkage 630 via a rotational joint 627, which has an axis of rotation coincident with the nominal axis of rotation of the proximal interphalangeal joints 644 of the anatomical hand. The axes of rotation can be viewed in FIG. 6B and FIG. 6C.

The four essential linkages 610, 620, 625, 630 (shown in FIG. 6A) of the hand movement assistance component 202 are actuated via at least one actuator 204 (as shown in FIGS. 6B and 6C), where the actuator is configured to rotate a pulley, and where the pulley is configured to actuate a first and second tendon, where rotation in a first direction winds the first tendon and unwinds the second, and rotation in the opposite direction does the opposite. In an exemplary embodiment, the actuator is a motor unit, where a motor unit consists of a motor, gearhead, two-way clutch, and double pulley. The two-way clutch enables self-locking, such that the tendon will be held in place within energizing the motor.

The actuator can be affixed to the plurality of linkages and rotatably coupled to the double pulley. A first pulley section can be wound with a first cable in the primary direction. A second pulley section can be wound with a second cable in an opposite direction. The first cable can pass along an anterior aspect of the plurality of linkages. The second cable can pass along a posterior aspect of the plurality of linkages.

In an exemplary embodiment, shown in FIG. 6A, the actuator 204 is a pair of motor units, the lateral motor unit 648 and the medial motor unit 649, where each motor unit actuates a pair of tendons. The lateral motor unit actuates a flexion tendon 652 (with path of tendon to actuator 204 indicated by dashed line in FIG. 6B) that passes through the lateral side of the hand device on the anterior aspect of joints 622 and 624 to flex the lateral side of the hand, and also actuates in a complementary manner an extension tendon 654 (with path of tendon to actuator 204 indicated by dashed line in FIG. 6B) that passes through the lateral side of the hand device on the posterior aspect of joints 622 and 624 to extend the lateral side of the hand. The medial motor unit 649 actuates a flexion tendon 656 (with path of tendon to actuator 204 indicated by dashed line in FIG. 6C) that passes through the medial side of the hand device on the anterior aspect of joints 623 and 625 to flex the medial side of the hand, and also actuates in a complementary manner an extension tendon 658 (with path of tendon to actuator 204 indicated by dashed line in FIG. 6C) that passes through the medial side of the hand device on the posterior aspect of joints 623 and 625 to extend the medial side of the hand.

The use of independent medial and lateral connecting linkages 625 and 620, in combination with the independent use of medial and lateral motor units 649 and 648, and associated independent tendons 652, 654, 656, and 658, enables an ability for the hand to wrap conformally around objects of irregular geometry, and thus provides an important function for stably and securely grasping and handling objects. Specifically, the hand employs independent medial and lateral tendon actuation, and the use of independent medial and lateral linkages results in substantial torsional compliance in the hand device, the combination of which enables a considerable movement gradient between the medial and lateral digits when grasping irregularly-shaped objects, and thus provides stable, conformal grasps of various object geometries.

Since the hand movement assistance device 212 is intended to be used by an individual with hemiparesis, it is desirable for the user to don and doff the device using their single unaffected hand and arm in a short period of time, and with minimal difficulty. In an exemplary embodiment, the process of quickly and easily donning and doffing the hand portion is facilitated by digit securing elements 210 that include quick-connect features. An exemplary set of quick connect features is comprised of a base containing at least one groove, and a mating set of clips that clip into the at least one groove in the base to secure the base to the clips. FIGS. 7A-7D show digit-securing elements with an exemplary set of quick-connect features. FIGS. 7C and 7D show how each digit can be secured via a finger strapping element 710, and each strapping element is affixed to a quick-connect base feature.

In an exemplary embodiment, the finger strapping element is a flexible finger cup. The finger strapping element is affixed to a quick-connect base 720 as shown in FIG. 7B. In this exemplary embodiment, the quick-connect base 720 is a convex plate that includes a pair of grooves oriented along the finger, one on the medial side of the finger (the medial groove 724 and one on the lateral side (the lateral groove 727).

Figure 7A:
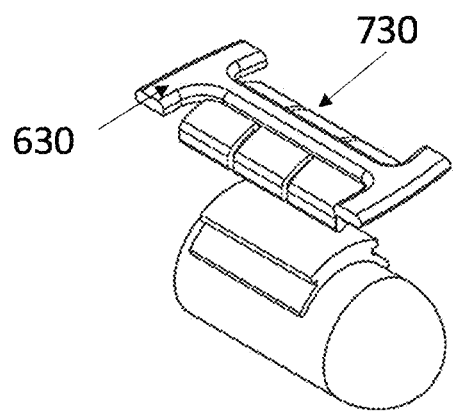
FIG. 7A-7D show a schematic diagrams of hand digit-securing elements according to an embodiment of the present disclosure.
Figure 7B:
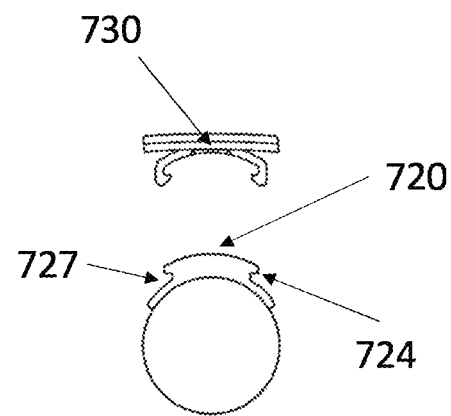
Figure 7C:
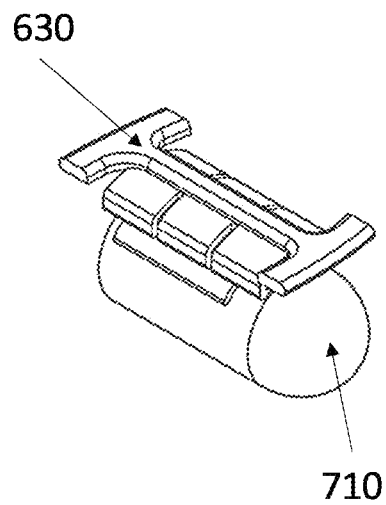
Figure 7D:
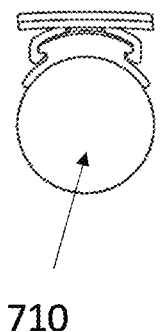

For each digit securing element, a mating set of clips 730 are attached to the distal phalange linkage 630 as shown in FIG. 7A. Since the mating clips 730 are flexible, they will deflect when the base 720 is pushed into them, then lock securely around the medial and lateral grooves once the base is pushed fully into the clips, such that the digit securing element will be securely affixed to the distal phalange linkage. FIGS. 7A-7D show both an isometric and frontal plane view of the quick-connect digit securing element, both in the unattached state as in FIGS. 7A and 7B and in the fully attached state as in FIGS. 7C and 7D. The clips 730 are also shown within the distal phalange linkage 630 in FIG. 6A. In an exemplary embodiment, the quick-connect base and mating clips are configured such that the base can be slidably moved in the axial (i.e., proximal or distal) direction to be released from the mating clips. Using this exemplary embodiment of quick-connect digit securing elements, a user would don the hand portion as follows. First insert each individual finger cup onto each respective fingertip; next place his or her hand into the open hand movement assistance device; and finally individually snap each quick-connect base 720 associated with each digit securing element into each respective set of mating clips 730. As such, each finger is independently snapped into place. In order to doff the hand portion, since the quick-connect base and mating clips are configured such that the base is released when slid in the proximal direction, the user can unstrap his or her arm from the arm portion, and subsequently slide the fingers proximally relative to the hand portion, thus releasing all quick-connect digit securing elements. The user can subsequently remove each of the finger cup from each fingertip. As such, the quick-connect features enable donning and doffing of the hand portion in a rapid manner and with minimal difficulty.

A user must be able to command opening and closing of the hand movement assistance device 202. Although use of electromyogram (EMG) from the affected arm could potentially be used to open and close the hand movement assistance device, such EMG is typically substantially impaired due to the hemiparesis, if present at all. As such, it is desirable to have a means of opening and closing that does not require EMG.

Since the orthotic device 100 is intended to be used by an individual with hemiparesis, the unaffected hand and arm can be used to command opening and closing of the hand movement assistance device. In this case, the control must be simple, and allow both control from the unaffected arm, and also still allow bimanual interaction between the unaffected and affected hands. The control must also be simple, since individuals who have had stroke may also have receptive aphasia, making it difficult for them to follow instructions. As such, the device must be usable and controllable using the single unaffected arm, in a simple manner, and also allow the individual to use his or her unaffected hand and arm to pass objects to and from the affected hand. Specifically, it is desirable for the user to use his or her unaffected hand both to activate opening and closing of the hand movement assistance device 202, and also to use the same unaffected hand to either pass objects to the affected hand prior to the hand movement assistance device closing, or to take objects from the affected hand prior to the hand movement assistance device opening.

Figure 8A:
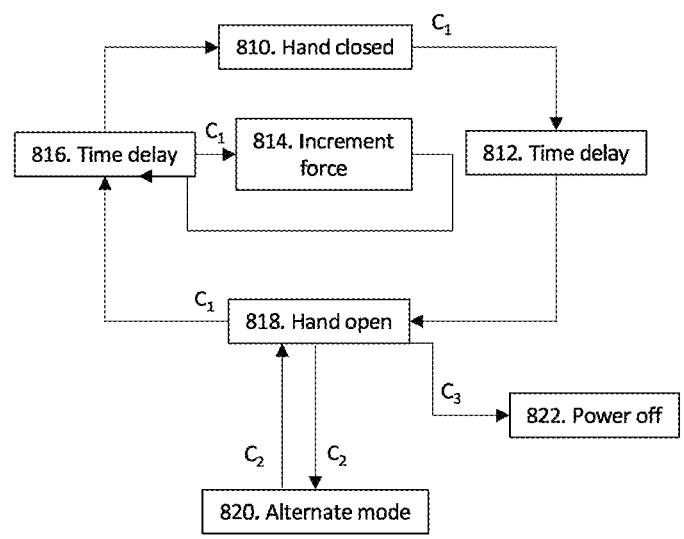
FIG. 8A shows a state chart of exemplary hand control functionality according to an embodiment of the present disclosure.

A state chart of exemplary hand control functionality according to an embodiment of the present disclosure is shown in FIG. 8A, where the condition $C_1$ indicates that the momentary switch is activated for a brief period of time (e.g., less than 2 seconds); $C_2$ indicates that the momentary switch is activated for a slightly longer period of time (e.g., between 5 and 10 seconds); and the condition $C_3$ indicates that the momentary switch is activated for a longer period still (e.g., more than 10 seconds). Note that LED, tactile, audible indicator, or other form of indicia can be used to provide feedback to the user regarding the duration of switch activation and ensuing control action, which is particularly useful, given the time-delayed movement of the device.

If the hand is closed in state 810 and condition $C_1$ is satisfied, the controller can send control signals to cause the hand to open into state 818 after a time delay through state 812. If the hand is opened in state 818 and condition $C_1$ is satisfied, the controller can send signals to close the hand into state 810 after a time delay through state 816. If, before the time delay period of state 816 is completed, condition $C_1$ is satisfied, the controller can send commands to increment the closing force according to state 814. The incrementing of the closing force of state 814 can occur proportionally to the number of times that condition $C_1$ is satisfied before the time delay of state 816 completes.

If the hand is opened in state 818 and condition $C_2$ is satisfied, the controller can send signals to transition the powered hand into an alternate mode in state 820. If the hand is opened in state 818 and condition $C_3$ is satisfied, the controller can send signals to power off the device into state 822.

In addition to these constraints, the controller can have a key for momentary interactions with the momentary switch. For examples, if the momentary switch is activated for a time less than a first time period, then condition $C_0$ is satisfied which translates to no change in the device. If the momentary switch is activated for a length of time between $t_1$ and $t_2$, then condition $C_1$ is satisfied. If the momentary switch is activated for a length of time between $t_2$ and $t_3$, then condition $C_2$ is satisfied. If the momentary switch is activated for a length of time longer than $t_3$, then condition $C_3$ is satisfied.

Figure 8B:
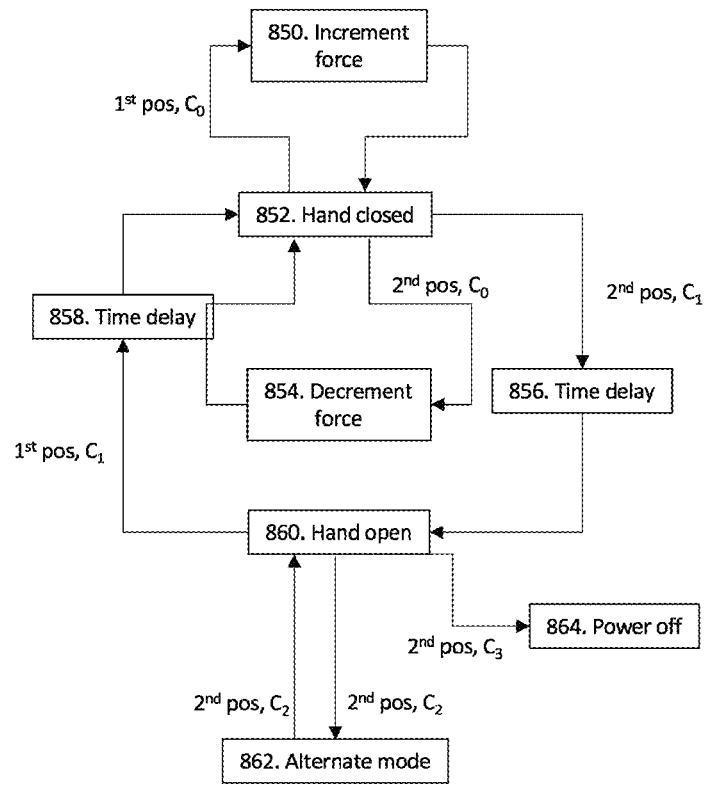
FIG. 8B a state chart of an exemplary control structure according to an embodiment of the present disclosure.

FIG. 8B provides a state chart of an exemplary control structure according to an embodiment of the present disclosure. This state chart describes possible interactions for a toggle switch. The condition $C_0$ indicates that the momentary switch is activated for a brief period of time (e.g., less than 2 seconds); the condition $C_1$ indicates that the momentary switch is activated for a somewhat longer period of time (e.g., between 2 and 5 seconds); $C_2$ indicates that the momentary switch is activated for a slightly longer period of time (e.g., between 5 and 10 seconds); and the condition $C_3$ indicates that the momentary switch is activated for a longer period still (e.g., more than 10 seconds). Note that LED, tactile, or audible indicators can be used to provide feedback to the user regarding the duration of switch activation and ensuing control action, which is particularly useful, given the time-delayed movement of the device.

If the hand is closed in state 852 and the toggle switch is moved into a first position for a length of time less than $t_1$, then condition $C_0$ is satisfied and a controller can be configured to increment the force in state 850 with which the hand closes in state 852. If the hand is closed in state 852 and the toggle switch is moved into a second position for a length of time less than $t_1$, then condition $C_0$ is satisfied and a controller can be configured to decrement the force through state 854 with which the hand closes into state 852. If the hand is closed in state 852 and the toggle switch is moved into a second position for a length of time between $t_1$ and $t_2$, then condition $C_1$ is satisfied and the controller can be configured to open the hand into state 860 with a time delay through state 856.

If the hand is open in state 860 and the toggle switch is moved into a first position for a length of time between $t_1$ and $t_2$, then condition $C_1$ is satisfied and the controller can be configured to close the hand into state 852 with a time delay through state 858. If the hand is open in state 860 and the toggle switch is moved into a second position for a length of time between $t_2$ and $t_3$, then condition $C_2$ is satisfied and the controller can be configured to alternate a control mode of the powered hand in state 862. The alternate control mode of state 862 can also be ended if the toggle switch is moved into a second position for a length of time between $t_2$ and $t_3$ so as to satisfy condition $C_2$.

If the hand is open in state 860 and the toggle switch is moved into a second position for a length of time greater than $t_3$, then condition $C_3$ is satisfied and the controller can be configured to power off the device into state 864.

The state chart of FIG. 8B can follow the same key for momentary interactions with the momentary switch as the key provided in FIG. 8A.

Figure 9:
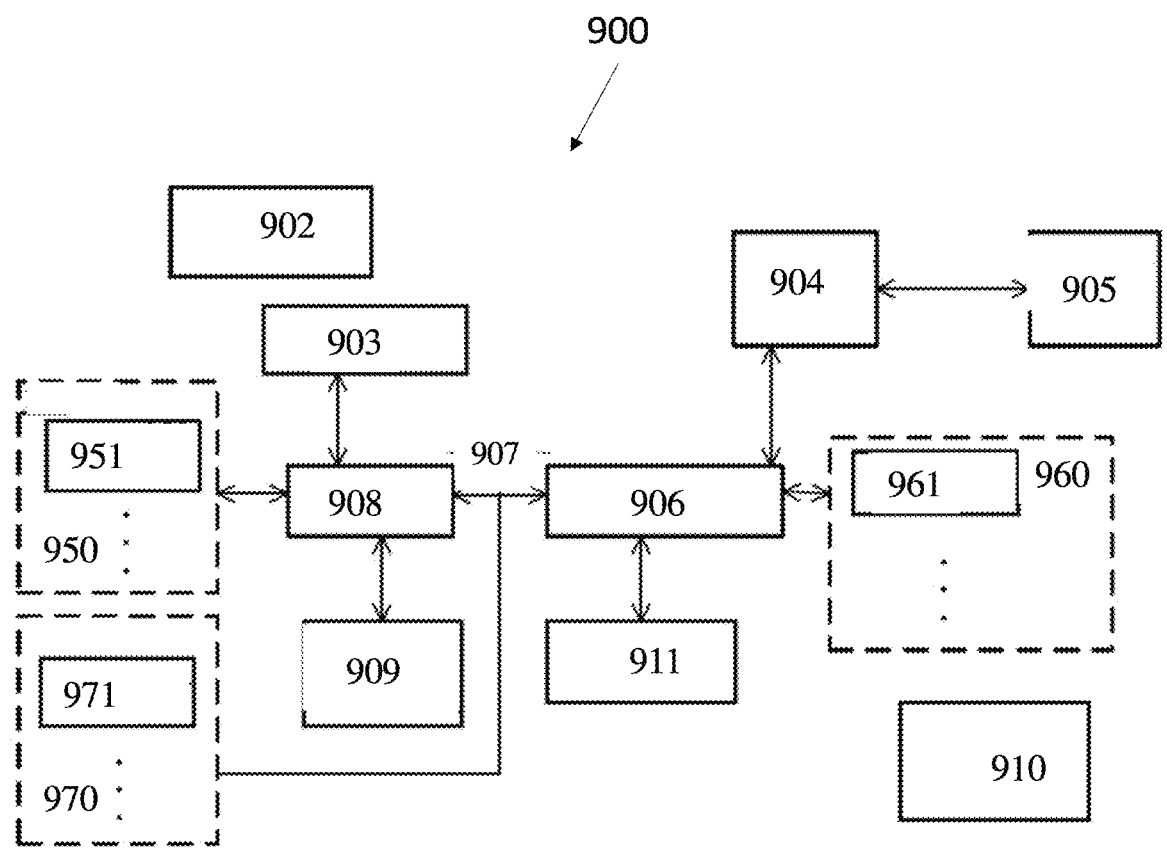
FIG. 9 is a schematic block diagram illustrating an exemplary system, in accordance with an implementation of the present disclosure.

FIG. 9 is a schematic block diagram illustrating an exemplary server system 900, in accordance with an implementation of the present disclosure. In this example, the server system 900 includes at least one microprocessor or processor 904; a BMC 903; one or more cooling modules 960; a main memory (MEM) 911; at least one power supply unit (PSU) 902 that receives an AC power from an AC power supply 901, and provides power to various components of the server system 900, such as the processor 904, north bridge (NB) logic 906, PCIe slots 960, south bridge (SB) logic 908, storage device 909, ISA slots 950, PCI slots 970, and BMC 903.

After being powered on, the server system 900 is configured to load software application from memory, a computer storage device, or an external storage device to perform various operations. The storage device 909 is structured into logical blocks that are available to an operating system and applications of the server system 900. The storage device 909 is configured to retain server data even when the server system 900 is powered off.

In FIG. 9, the memory 911 is coupled to the processor 904 via the NB logic 906. The memory 911 may include, but is not limited to, dynamic random access memory (DRAM), double data rate DRAM (DDR DRAM), static RAM (SRAM), or other types of suitable memory. The memory 911 can be configured to store firmware data of the server system 900. In some configurations, firmware data can be stored on the storage device 909.

In some implementations, the server system 900 can further comprise a flash storage device. The flash storage device can be a flash drive, a random access memory (RAM), a non-volatile random-access memory (NVRAM), or an electrically erasable programmable read-only memory (EEPROM). The flash storage device can be configured to store system configurations such as firmware data.

The processor 904 can be a central processing unit (CPU) configured to execute program instructions for specific functions. For example, during a booting process, the processor 904 can access firmware data stored in the BMC 903 or the flash storage device, and execute the BIOS 905 to initialize the server system 900. After the booting process, the processor 904 can execute an operating system in order to perform and manage specific tasks for the server system 900.

In some configurations, the processor 904 can be multi-core processors, each of which is coupled together through a CPU bus connected to the NB logic 906. In some configurations, the NB logic 906 can be integrated into the processor 904. The NB logic 906 can also be connected to a plurality of peripheral component interconnect express (PCIe) slots 960 and an SB logic 908 (optional). The plurality of PCIe slots 960 can be used for connections and buses such as PCI Express x1, USB 2.0, SMBus, SIM card, future extension for another PCIe lane, 1.5 V and 3.3 V power, and wires to diagnostics LEDs on the server system 900's chassis.

In system 900, the NB logic 906 and the SB logic 908 are connected by a peripheral component interconnect (PCI) Bus 907. The PCI Bus 907 can support functions on the processor 904 but in a standardized format that is independent of any of the processor 904's native buses. The PCI Bus 907 can be further connected to a plurality of PCI slots 970 (e.g., a PCI slot 971). Devices connect to the PCI Bus 907 may appear to a bus controller (not shown) to be connected directly to a CPU bus, assigned addresses in the processor 904's address space, and synchronized to a single bus clock. PCI cards that can be used in the plurality of PCI slots 970 include, but are not limited to, network interface cards (NICs), sound cards, modems, TV tuner cards, disk controllers, video cards, small computer system interface (SCSI) adapters, and personal computer memory card international association (PCMCIA) cards.

The SB logic 908 can couple the PCI Bus 907 to a plurality of expansion cards or ISA slots 950 (e.g., an ISA slot 951) via an expansion bus. The expansion bus can be a bus used for communications between the SB logic 908 and peripheral devices, and may include, but is not limited to, an industry standard architecture (ISA) bus, PC/904 bus, low pin count bus, extended ISA (EISA) bus, universal serial bus (USB), integrated drive electronics (IDE) bus, or any other suitable bus that can be used for data communications for peripheral devices.

In this example, BIOS 905 can be any program instructions or firmware configured to initiate and identify various components of the server system 900. The BIOS is an important system component that is responsible for initializing and testing hardware components of a corresponding server system. The BIOS can provide an abstraction layer for the hardware components, thereby providing a consistent way for applications and operating systems to interact with a peripheral device such as a keyboard, a display, and other input/output devices.

In system 900, the SB logic 908 is further coupled to the BMC 903 that is connected to the PSU 902. In some implementations, the BMC 903 can also be a rack management controller (RMC). The BMC 903 is configured to monitor operation status of components of the server system 900, and control the server system 900 based upon the operation status of the components.

Although only certain components are shown within the exemplary systems 900 in FIG. 9, various types of electronic or computing components that are capable of processing or storing data, or receiving or transmitting signals, can also be included in the exemplary system 900. Further, the electronic or computing components in the exemplary system 900 can be configured to execute various types of application, and/or can use various types of operating systems. These operating systems can include, but are not limited to, Android, Berkeley Software Distribution (BSD), iPhone OS (iOS), Linux, OS X, Unix-like Real-time Operating System (e.g., QNX), Microsoft Windows, Window Phone, and IBM z/OS.

Depending on the desired implementation for the exemplary systems 900, a variety of networking and messaging protocols can be used, including but not limited to TCP/IP, open systems interconnection (OSI), file transfer protocol (FTP), universal plug and play (UpnP), network file system (NFS), common internet file system (CIFS), AppleTalk etc. As would be appreciated by those skilled in the art, FIG. 9 is used for purposes of explanation. Therefore, a network system can be implemented with many variations, as appropriate, yet still provide a configuration of network platform in accordance with various examples of the present disclosure.

In exemplary configurations of FIG. 9, the exemplary system 900 can also include one or more wireless components operable to communicate with one or more electronic devices within a computing range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections, as known in the art. Various other elements and/or combinations are possible as well within the scope of various examples.

EXAMPLES

Clutch Mechanism Embodiments

The electrically-actuated clutch mechanism can include at least one rotating member, at least one sliding member, and at least one bearing member. The rotating member can be affixed to a first arm section. The sliding member can slide through a second arm section, such that the rotating member rotates relative to the sliding member. The first arm section can be either the upper arm section or forearm section. The second arm section can be the corresponding arm section. The rotating member can be configured to include at least one detent. The sliding member can be slidably configured within the second arm section into either a first slider position or a second slider position. The at least one bearing member can be positioned between the rotating member and the sliding member. In the first slider position, the sliding member forces the at least one bearing member into the at least one detent in the rotating member. In the second slider position, the sliding member releases the at least one bearing member from the detent in the rotating member. The at least one bearing member can be cylindrical or spherical in shape.

In some embodiments, the at least one sliding member can be axisymmetric with a first end and a second end connected by a center section. The first end can have a larger diameter than the second end. The center section can have a variable diameter that transitions from the diameter of the first end to the diameter of the second end.

Orthotic Device with Elbow and Wrist Clutch

In some embodiments, the orthotic device can have both an elbow and wrist clutch. The orthotic device can include a first and a second electrically-actuated clutch mechanism. The device can comprise a first, second, and third arm section. The first electrically-actuated clutch mechanism can be comprised of at least one rotating member, at least one sliding member, and at least one bearing member. The rotating member can be affixed to the first arm section and the sliding member can slide through the second arm section, such that the rotating member rotates relative to the sliding member. The rotating member can be configured to include at least one detent. The sliding member can be slidably configured within the second arm section into either a first slider position or a second slider position. The at least one bearing member can be positioned between the rotating member and the sliding member. In the first slider position, the sliding member can force the at least one bearing member into the at least one detent in the rotating member. In the second slider position, the sliding member can release the at least one bearing member from the detent in the rotating member.

The second electrically-actuated clutch mechanism can include at least a first and a second sliding member and at least one bearing member. The first sliding member can be affixed to the third arm section. The first sliding member can comprise a constant-radius curvilinear shape and slide through a corresponding constant-radius curvilinear channel in the second arm section. The second sliding member can slide through the second arm section, such that the first sliding member rotates relative to the second sliding member. The first sliding member can be configured to include at least one detent. The second sliding member can be slidably configured within the second arm section into either a first slider position or a second slider position. The at least one bearing member can be positioned between the first sliding member and the second sliding member. In the first slider position, the second sliding member can force the at least one bearing member into the at least one detent in the first sliding member. In the second slider position, the second sliding member can release the at least one bearing member from the detent in the first sliding member.

In some examples, the curvilinear first sliding member can be located proximally on the forearm.

In some examples, the at least one sliding member of the first electrically-actuated clutch mechanism and the second sliding member of the second electrically-actuated clutch mechanism can slide along coincident axes. The sliding members can be actuated by a common solenoid actuator.

Hand Portion Linkages

The hand portion can be operable through independent medial and lateral links. A possible listing of the plurality of linkages for a hand portion follows. The plurality of linkages can include at least a first, second, third, and fourth linkage. The first linkage can be adjoined to the posterior aspect of the metacarpal portion of a subject's hand. The fourth linkage can be adjoined to the posterior aspect of the middle and distal phalange portion of the subject's hand. The second linkage can be adjoined to the medial aspect of the proximal phalanges portion of the hand and can be comprised of a proximal end and a distal end. The proximal end of the second linkage can be rotatably coupled to the first linkage on the medial aspect of the subject's hand. A corresponding axis of rotation of the second linkage can be nominally coincident with an axis of rotation of the metacarpal phalangeal joints of the subject's hand. The distal end of the second linkage can be rotatably coupled to the fourth linkage on the medial aspect of the subject's hand. A corresponding axis of rotation of the fourth linkage is nominally coincident with an axis of rotation of the proximal interphalangeal joints of the subject's hand. The third linkage can be adjoined to the lateral aspect of the proximal phalanges portion of the subject's hand and can be comprised of a proximal end and a distal end. The proximal end of the third linkage can be rotatably coupled to the first linkage on the lateral aspect of the subject's hand. A corresponding axis of rotation can be nominally coincident with an axis of rotation of the metacarpal phalangeal joints of the subject's hand. The distal end of the third linkage can be rotatably coupled to the fourth linkage on the lateral aspect of the subject's hand. A corresponding axis of rotation can be nominally coincident with an axis of rotation of the proximal interphalangeal joints of the subject's hand.

A hand portion configured as such can have bidirectional tendon actuation enabled by at least one powered actuator. The at least one powered actuator is at least one electric motor affixed to the first hand linkage. The electric motor can be rotatably coupled to at least one double pulley with a first pulley section and a second pulley section. The first pulley section can be wound with a first cable in one direction. The second pulley section can be wound with a second cable in the opposite direction. The first cable can pass through channels along the anterior aspect of the first, second, and third hand linkages and can be affixed to the fourth hand linkage. The second cable can pass through channels along the posterior aspect of the first, second, and third hand linkages and can be affixed to the fourth hand linkage.

The first cable can consist of a medial and lateral cable. The first medial cable can pass through channels along an anterior aspect of the first and second hand linkages on the medial aspect of the subject's hand. The first medial cable can be affixed to the medial aspect of the fourth hand linkage. The first lateral cable can pass through channels along an anterior aspect of the first and third hand linkages on the lateral aspect of the subject's hand. The first lateral cable can be affixed to the lateral aspect of the fourth hand linkage. The second cable can consist of a medial and lateral cable. The second medial cable can pass through channels along the posterior aspect of the first and second hand linkages on the medial aspect of the subject's hand. The second medial cable can be affixed to the medial aspect of the fourth hand linkage. The second lateral cable can pass through channels along the posterior aspect of the first and third hand linkages on the lateral aspect of the hand. The second lateral cable can be affixed to the lateral aspect of the fourth hand linkage.

In some embodiments, the device of claim 51, where the at least one electric motor can be two electric motors: a medial electric motor and a lateral electric motor. The medial electric motor can actuate the first and second medial cables. The lateral electric motor can actuate the first and second lateral cables. In some examples, the at least one pulley can be rotatably coupled to the at least one electric motor through a two-way roller clutch.

Quick-Connect Finger Cups

The plurality of linkages of the hand portion can comprise at least a distal linkage adjoined to a posterior aspect of a distal phalange portion of the subject's hand. The orthotic device can further include at least one digit securing element. The digit securing element can be comprised of at least a strapping element and a quick-connect base element. The quick-connect base element can be comprised of a convex surface that can be snapped into a mating set of receiving clips in the distal linkage in a quick-connect manner.

In some examples, the quick-connect features in the digit securing element can be released from the distal linkage by sliding the digit securing element proximally relative to the distal linkage. The strapping element can be a finger cup.

Thumb Cup and Rod Embodiments

The plurality of linkages in the hand portion can comprise at least a first linkage adjoined to the posterior aspect of the metacarpal portion of the hand. The thumb portion can comprise at least a thumb cup and a thumb rod. The thumb rod can comprise a first end and a second end. The first end can be clamped slidably and rotatably to the first linkage. The second end can be clamped slidably and rotatably to the thumb cup.

The plurality of linkages in the hand portion can comprise at least a first linkage adjoined to a posterior aspect of the metacarpal portion of the subject's hand. The thumb portion can comprise at least a thumb cup and a thumb rod. The thumb rod can comprise a first end and a second end. The second end of the thumb rod can be clamped slidably and rotatably to the thumb cup. The first end of the thumb rod can be rotatably coupled to the first linkage. The rotatable coupling can contain at least one detent that retains the thumb rod in a desired configuration, such that the thumb rod can be manually repositioned between detent orientations.

Data on Grasping Force

Figure 10A:
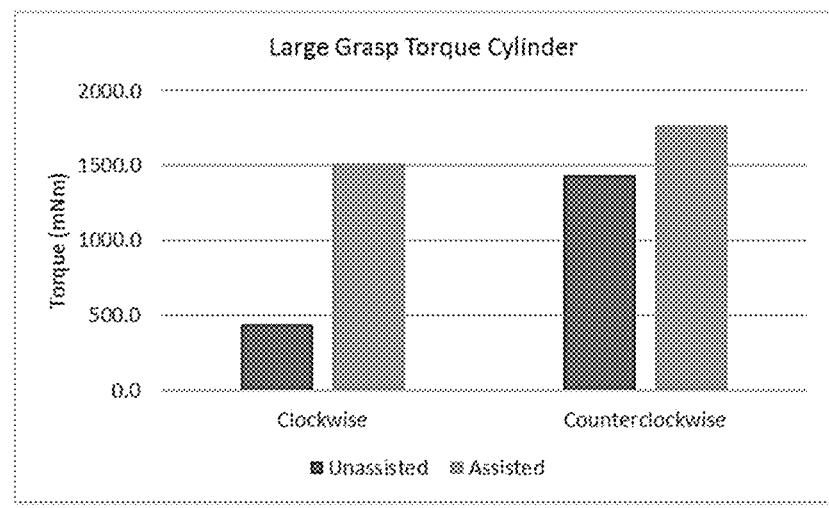
FIGS. 10A-10B compares the ability of individuals to exert torque when grasping cylinders with different diameters as compared between unassisted individuals and individuals assisted with an orthotic device according to an embodiment of the present disclosure.
Figure 10B:
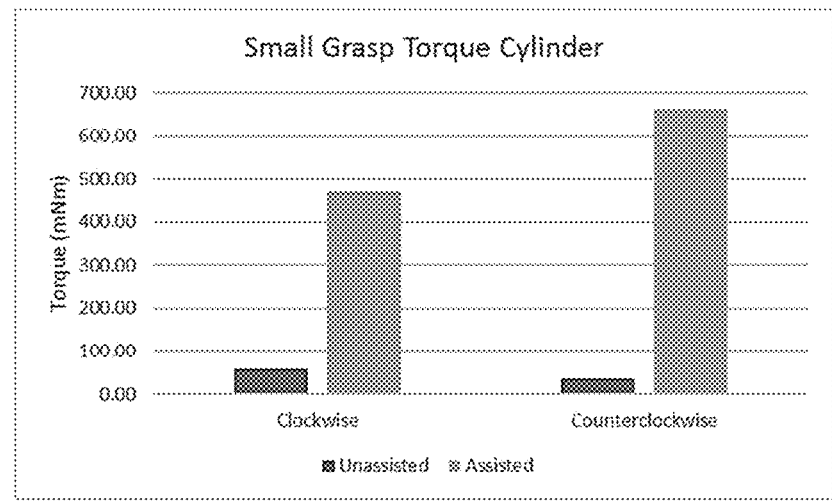

FIGS. 10A-10B compare the ability of an individual with hemiparesis (from stroke) to exert torque when grasping cylinders of different diameters with and without use of an orthotic device according to an embodiment of the present disclosure. The data characterizes the large-object (FIG. 10A) and small-object (FIG. 10B) grasp force, respectively, with and without the exoskeleton. On average, the orthotic device increased the large-object grasp force by almost a factor of two, while the device increased the small-object grasp force by a factor of twelve. Note that subjects with strong passive tone are capable of some degree of passive grasping (due to muscle tone rather than muscle contraction), which explains the substantial improvements in small-object grasp force relative to large-object grasp force. Nonetheless, even with the large objects, the device doubled the grasp force.

Bottle Opening

Figure 11A:
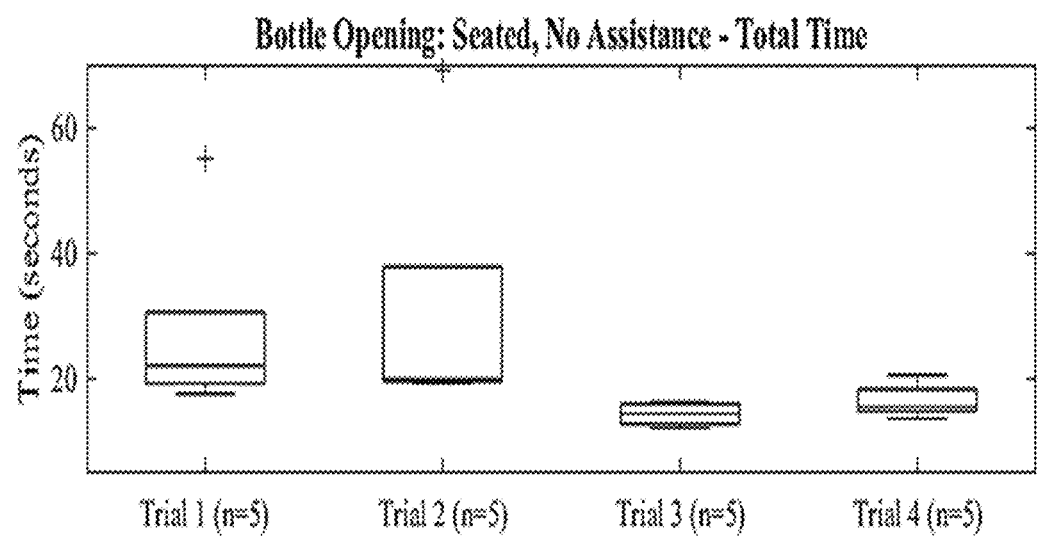
FIGS. 11A-11D show how long it takes for individuals to open a bottle and compares the times of individuals unassisted with an orthotic device to individuals assisted with an orthotic device according to an embodiment of the present disclosure.
Figure 11B:
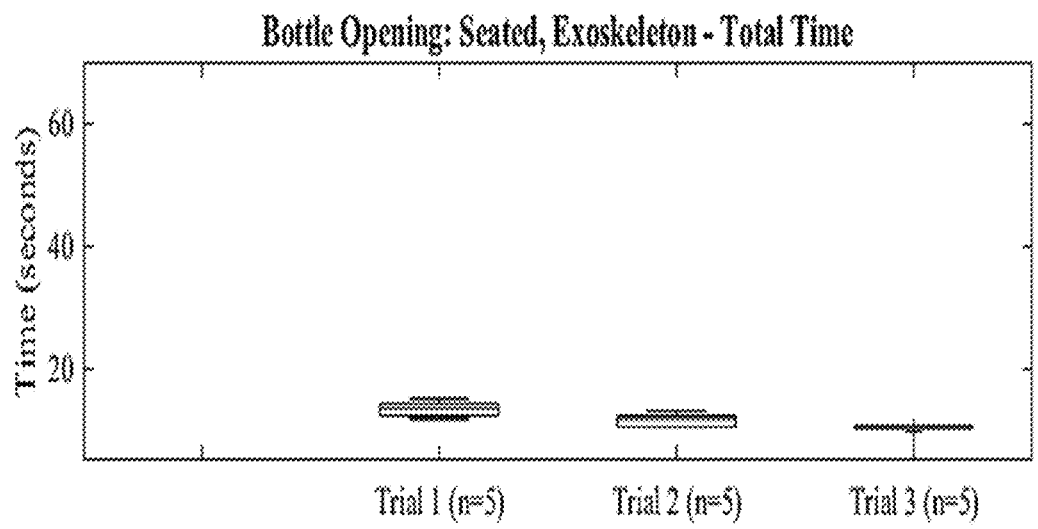

FIGS. 11A and 11B show total times for opening a bottle in a seated position without and with, respectively, a device according to the various embodiments. These results show that the seated subject was on average able to open a bottle while seated twice as fast when wearing the device relative to without it, and recorded no spills with the device, while they spilled the contents 20% of the time without it. This shows the effectiveness of an orthotic device according to an embodiment of the present disclosure for assisting with daily tasks such as opening a bottle.

Figure 11C:
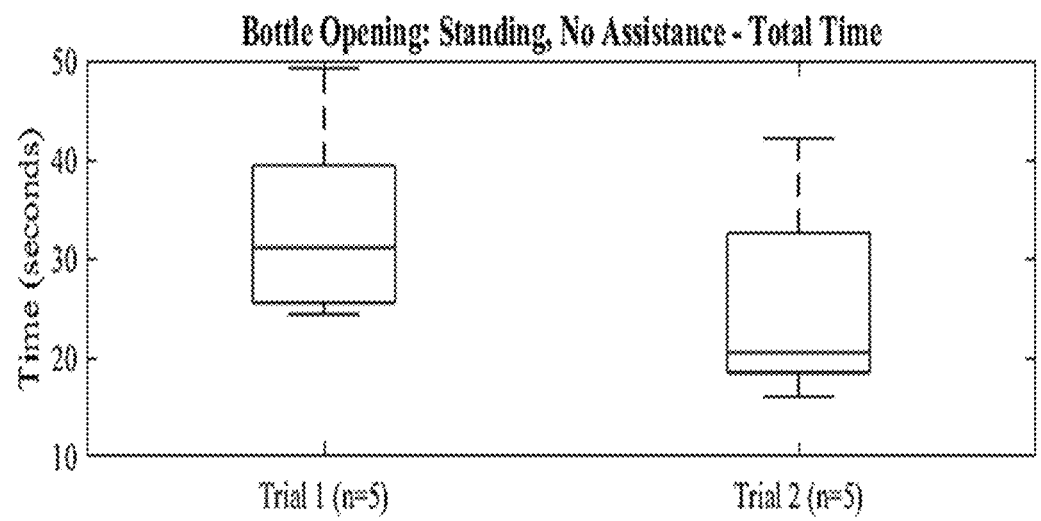
Figure 11D:
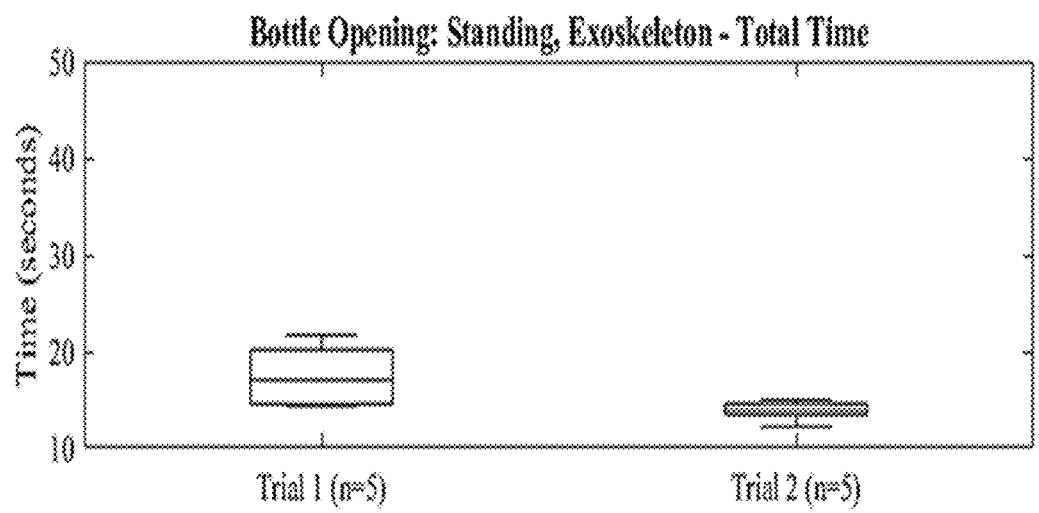

FIGS. 11C and 11D show total times for opening a bottle without and with, respectively, a device according to the various embodiments while standing (i.e., subject could not use a table to support the bottle). On average, the subject was able to complete the task (opening a bottle) five times faster when wearing the device, relative to without it. Further, the subject had no spills with the device, but spilled 10% of the time without it.

Bread Cutting

Figure 12A:
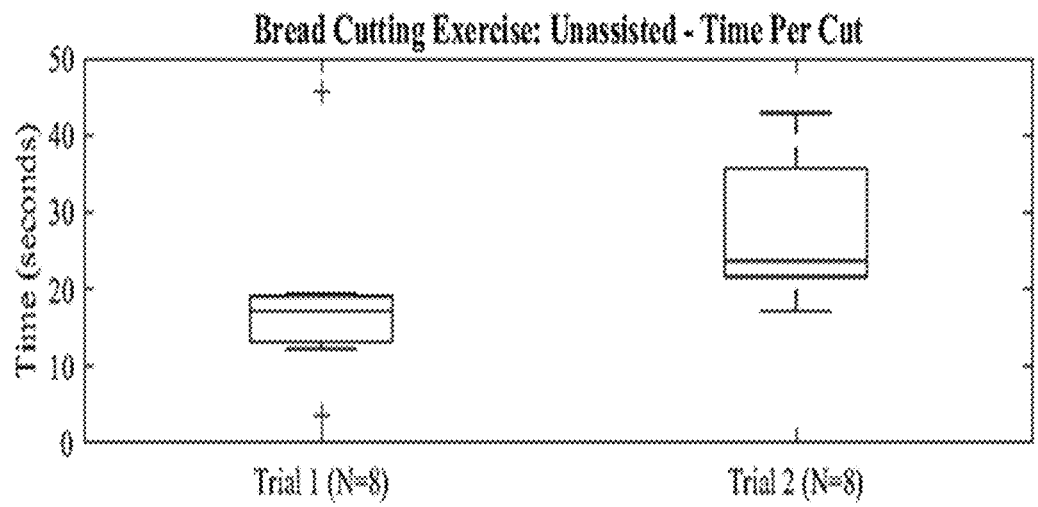
FIGS. 12A-12B show how long it takes for individuals to slice bread and compares the times of individuals unassisted with an orthotic device to individuals assisted with an orthotic device according to an embodiment of the present disclosure.
Figure 12B:
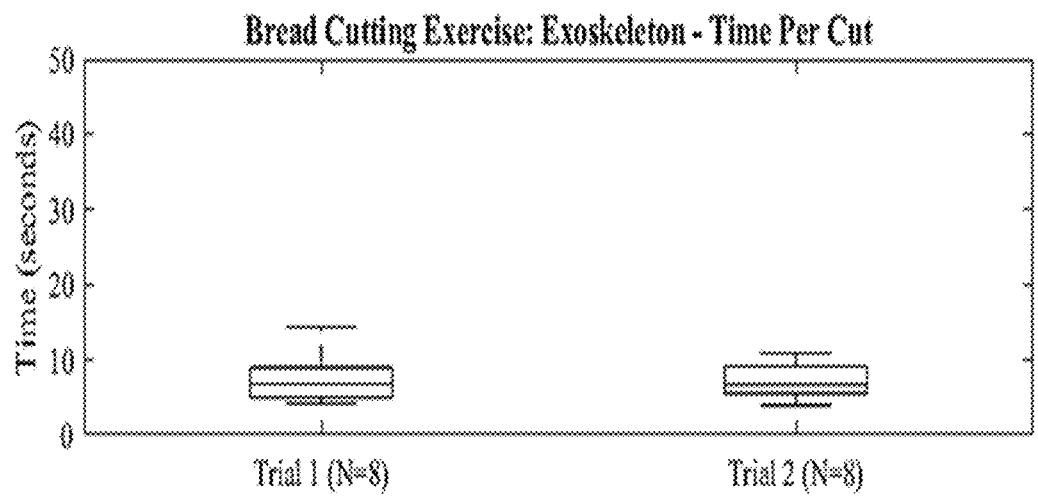

FIGS. 12A and 12B show total times for slicing bread without and with, respectively, a device according to the various embodiments. These results demonstrate the effectiveness of the device for performing daily tasks. In particular, the results show the time required to cut ten slices of bread without and with the device. As per the data, the subject was on average able to slice bread four times faster with exoskeleton, and qualitatively produced superior results when wearing it.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. An orthotic device, comprising:
an upper arm section;
a forearm section;
at least one elbow joint rotatably coupling the upper arm section and the forearm section; and
at least one electrically-actuated clutch mechanism comprised of at least one rotating member, at least one sliding member, and at least one bearing member wherein the at least one electrically-actuated clutch mechanism further comprises: the at least one rotating member includes at least one detent and is affixed to a first arm section; and the at least one sliding member slides through a second arm section, such that the at least one rotating member rotates relative to the at least one sliding member; the at least one sliding member is slidably configured within the second arm section into either a first slider position or a second slider position; wherein in the first slider position, the at least one sliding member forces the at least one bearing member into the at least one detent in the rotating member; and wherein in the second slider position, the sliding member releases the at least one bearing member from the at least one detent in the at least one rotating member and wherein the at least one sliding member is configured into the first slider position by a spring and configured into the second slider position by energizing a solenoid actuator.

2. The device of claim 1, wherein the at least one detent is on a radial aspect of the at least one rotating member and is cylindrical or spherical in shape.

3. The orthotic device of claim 1, wherein the at least one rotating member is a clutch disc.

4. An orthotic device, comprising:
an upper arm section;
a forearm section;
at least one elbow joint rotatably coupling the upper arm section and the forearm section; and
at least one electrically-actuated elbow and wrist rotation clutch mechanism comprised of at least one rotating member and at least one sliding member, and at least one bearing member wherein the at least one electrically-actuated elbow and wrist clutch mechanism further comprises: the at least one rotating member includes at least one detent and is affixed to a first arm section; and the at least one sliding member slides through a second arm section, such that the at least one rotating member rotates relative to the at least one sliding member; the at least one sliding member is slidably configured within the second arm section into either a first slider position or a second slider position; wherein in the first slider position, the at least one sliding member forces the at least one bearing member into the at least one detent in the rotating member; and wherein in the second slider position, the sliding member releases the at least one bearing member from the at least one detent in the at least one rotating member and wherein the at least one sliding member is configured into the first slider position by a spring and configured into the second slider position by energizing a solenoid actuator.

5. The orthotic device of claim 4, wherein the at least one sliding member is a constant-radius curvilinear sliding member.

6. The orthotic device of claim 4, wherein the constant-radius curvilinear sliding member is affixed to the forearm section.

7. The orthotic device of claim 4, wherein the constant-radius curvilinear sliding member includes a plurality of detents.

* * * * *